(12) United States Patent
Sakamoto et al.

(10) Patent No.: US 8,790,280 B2
(45) Date of Patent: Jul. 29, 2014

(54) HUMAN STATE ESTIMATING DEVICE AND METHOD

(75) Inventors: Kiyomi Sakamoto, Nara (JP); Shoichi Aoyama, Osaka (JP); Shigeo Asahara, Osaka (JP); Xiaolin Zhang, Tokyo (JP); Hirohiko Kaneko, Tokyo (JP); Keiji Uchikawa, Kanagawa (JP); Haruki Mizushina, Kanagawa (JP); Naofumi Murata, Fukushima (JP); Koichi Tanaka, Kanagawa (JP)

(73) Assignee: Panasonic Corporation, Osaka (JP)

( * ) Notice: Subject to any disclaimer, the term of this patent is extended or adjusted under 35 U.S.C. 154(b) by 802 days.

(21) Appl. No.: 12/666,507

(22) PCT Filed: Jun. 25, 2008

(86) PCT No.: PCT/JP2008/001656
§ 371 (c)(1),
(2), (4) Date: Dec. 23, 2009

(87) PCT Pub. No.: WO2009/001558
PCT Pub. Date: Dec. 31, 2008

(65) Prior Publication Data
US 2010/0191156 A1    Jul. 29, 2010

(30) Foreign Application Priority Data

Jun. 27, 2007 (JP) ................................ 2007-169799

(51) Int. Cl.
| A61B 5/103 | (2006.01) |
| A61B 5/117 | (2006.01) |
| A61B 5/04 | (2006.01) |
| A61B 13/00 | (2006.01) |
| A61B 3/14 | (2006.01) |
| G06K 9/00 | (2006.01) |

(52) U.S. Cl.
USPC ........... 600/595; 600/544; 600/558; 351/209; 382/117

(58) Field of Classification Search
USPC ................. 600/544, 558, 595; 351/206, 209; 382/117; 434/258
See application file for complete search history.

(56) References Cited

U.S. PATENT DOCUMENTS

| 5,365,941 A | 11/1994 | Yoshimatsu et al. |
| 2003/0028121 A1 | 2/2003 | Blazey et al. |

(Continued)

FOREIGN PATENT DOCUMENTS

| JP | 6-154167 | 6/1994 |
| JP | 2003-33355 | 2/2003 |
| JP | 2005-124909 | 5/2005 |

OTHER PUBLICATIONS

Liang et al., "Scaling of Horizontal and Vertical Fixational Eye Movements", Physical Review E 71, 031909, Mar. 21, 2005, p. 1-6.*
International Search Report issued Jul. 22, 2008 in International (PCT) Application No. PCT/JP2008/001656.

*Primary Examiner* — Devin Henson
(74) *Attorney, Agent, or Firm* — Wenderoth, Lind & Ponack, L.L.P.

(57) ABSTRACT

To provide a human state estimating device which accurately estimates a human state. The human state estimating device includes: a storage unit (16) which stores reference data (17) in which a human state and a reference profile including a horizontal component of a standard microsaccade in the human state are corresponded to each other, for each of plural personal attribute information; a video obtaining unit (11) which obtains video of a user's eyeball, with an eyeball rotation angle accuracy of 0.05 degrees or higher, and a measuring speed of 120 samples per second or higher; an analyzing unit (12) which generates an actual-measurement profile including the horizontal component of the microsaccade, from fixational eye movement shown in the video; a personal attribute information obtaining unit (13) which obtains the user's personal attribute information; and an analyzing unit which estimates the human state by searching, in the reference data (17), for a reference profile that corresponds to the obtained personal attribute information and is closest to the actual-measurement profile.

9 Claims, 19 Drawing Sheets

(56) References Cited

U.S. PATENT DOCUMENTS

2003/0120172 A1 6/2003 Foust et al.
2005/0108092 A1* 5/2005 Campbell et al. ............... 705/14
2005/0113713 A1 5/2005 Foust et al.
2006/0202841 A1 9/2006 Johns
2008/0104415 A1* 5/2008 Palti-Wasserman et al. . 713/186

* cited by examiner

FIG. 4

| Psychological state | Emotional state | Thinking state |
|---|---|---|
| ⇩ | ⇩ | ⇩ |

Psychological state
0: Composure
1: Uncertainty
11: Uncertainty over the past (worry about past)
12: Situation uncertainty (Present)
13: Anticipatory anxiety
2: Confusion
21: Decision difficulty (Plural options)
22: Contradiction with memory
23: Case of no recollection
231: No concept
232: Unaware of operating procedure
233: Cannot understand stipulation
24: Case of misoperation (Irreversible)
3: Impatience/frustration
31: Under time pressure
32: Working on impossible task
33: Task not going as desired Emotional state
0: None
1: Pleasure/displeasure
11: Pleasure
12: Displeasure
2: Excitement/calmness axis
21: Excitement
22: Calm
3: Nervousness/relaxation axis
31: Nervous
32: Relaxed Thinking state
0: None
1: Mathematical task
2: Memory task
21: Episode
"What was yesterday's dinner?"
22: Knowledge
"When was the start of the Tokugawa Shogunate"
23: Implicit memory
"What was most recent dream about?"
22: Thinking task
3: Thinking task
31: Concept/thought generation construction
"In order to expand creativity"
32: Wisconsin card sorting test
4: Image manipulation task
41: Visual image manipulation
"Recall route up to home"
"Count appliances at home"
"Visualize mirror letter"
42: Auditory image manipulation
"Recall melody of one's favorite song" "Recall a nursery rhyme" "Recall sound of rubbing an aluminum plate with a fork"
43: Tactile image manipulation
44: Gustatory image manipulation "Recall taste of a lemon" "Recall taste of a pickled plum" "Recall taste of bear's stomach"
45: Olfactory image manipulation "Recall one's a favorite smell"

Region A  Region B

Center of choroid fissure

Center  Up  Down

Light intensity distribution

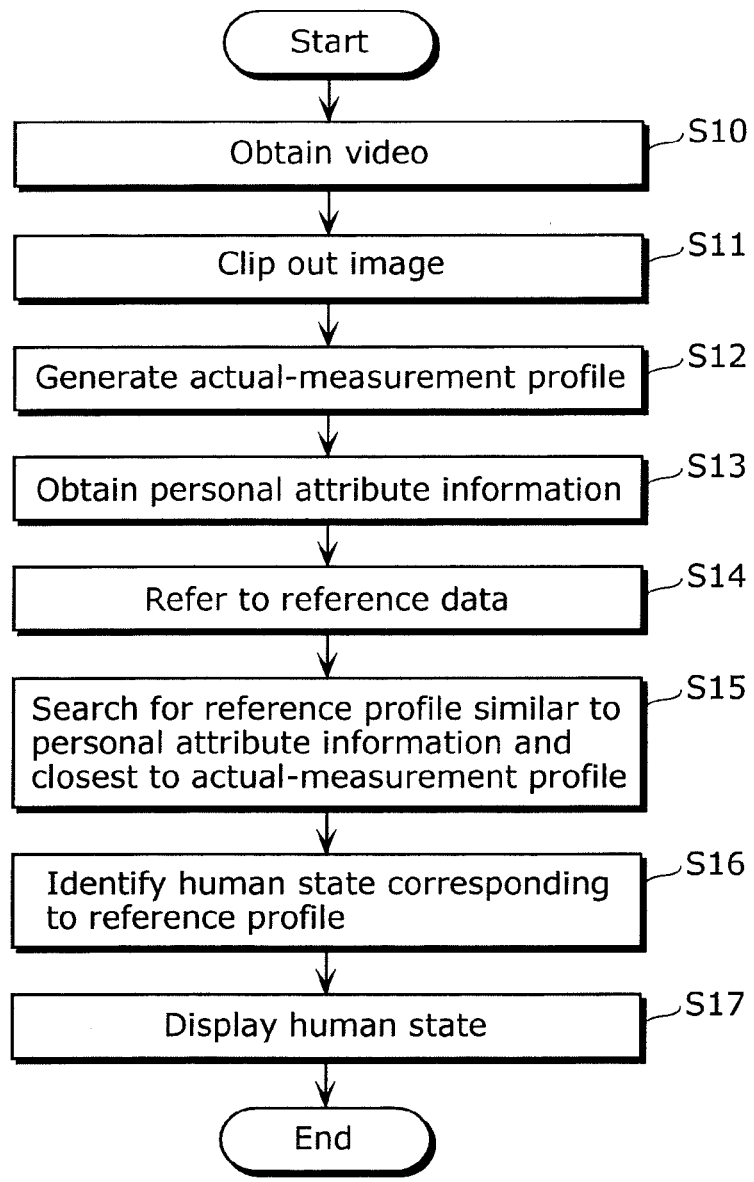

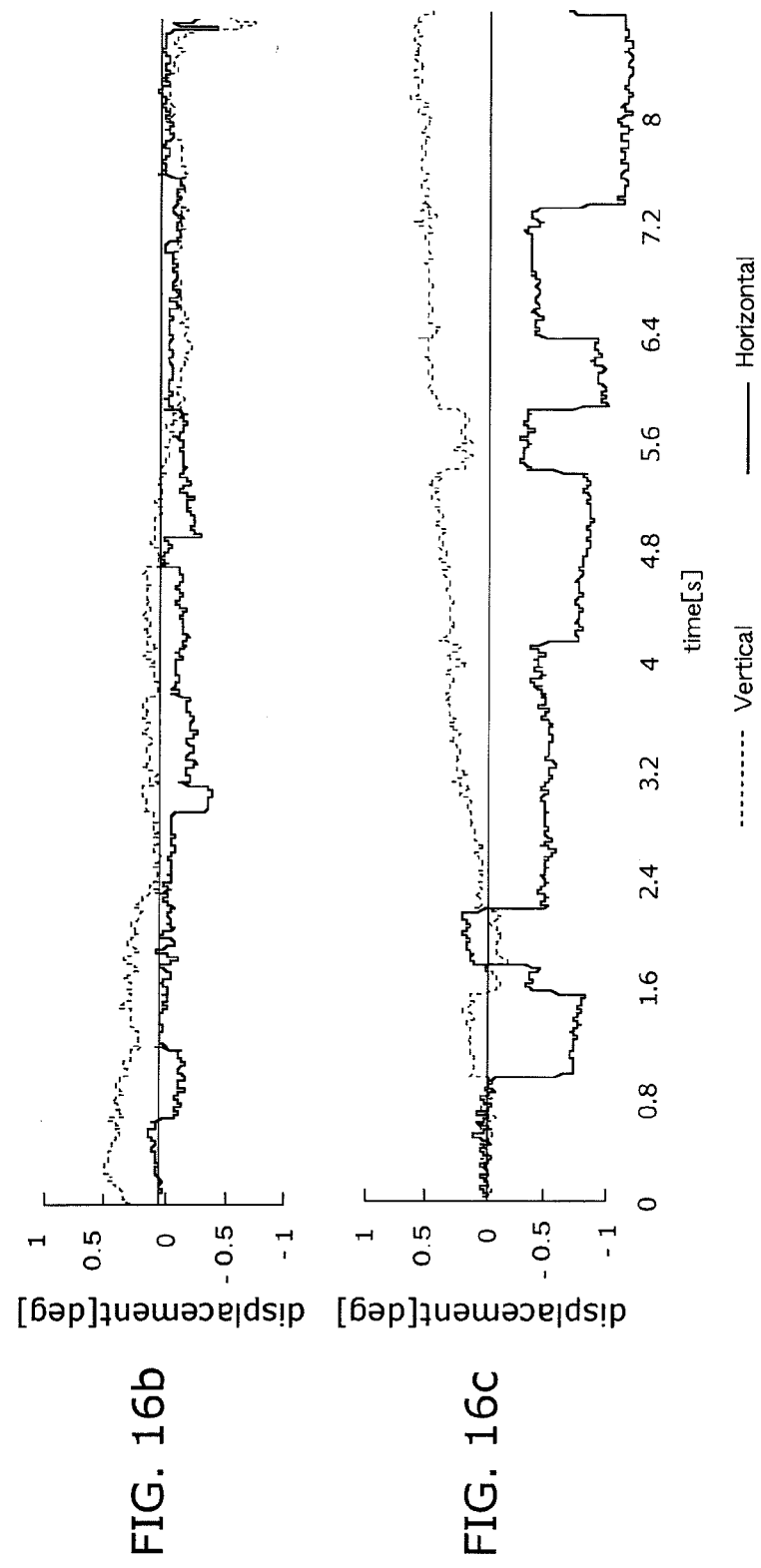
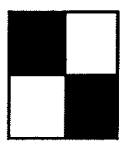
FIG. 16a
FIG. 16b
FIG. 16c

HUMAN STATE ESTIMATING DEVICE AND METHOD

TECHNICAL FIELD

The present invention relates to devices which estimate a human state such as a psychological state, an emotional state, and a thinking state, and particularly relates to a device which estimates a human state based on fixational eye movement of an eyeball of a human.

BACKGROUND ART

With the increase in functions, increase in complexity, and systemization of electronic devices represented by a digital television, methods and procedures for their use have become increasingly complex in recent years. In addition, with the diversification of a user's use situation and usage pattern, a Human-Machine Interface (HMI) that has been customized to suit the state of a person is in demand, and a device or method for accurately estimating and measuring a human state such as the psychological state, the emotional state, and the thinking state of the user is becoming a very important element.

Conventionally, there have been various attempts at estimating such human states (for example, see Patent Reference 1). Patent Reference 1 proposes a fixational eye movement checking device which detects the movement of an eyeball of a subject when indices are presented on an index board, and distinguishes an abnormality in the fixational eye movement component from the time variation in the line of sight movement based on the detected eyeball movement, so as to determine a brain function-related disorder. This device checks for abnormalities in the eyeball movement control mechanism in the brain of the subject by measuring and analyzing the fixational eye movement of an eyeball of the subject, and thereby facilitates the distinguishing of cerebrovascular dementia, and so on.

It should be noted that "fixational eye movement" is one type of eyeball movement, and is the fine trembling of the eye which occurs involuntarily at all times even when staring at a still object.

Patent Reference 1: Japanese Unexamined Patent Application Publication No. 06-154167

SUMMARY OF THE INVENTION

Problems that Invention is to Solve

However, with the fixational eye movement checking device disclosed in aforementioned Patent Reference 1, there is the problem that, even when a brain function-related disorder can be determined, human states such as the psychological state, the emotional state, and the thinking state cannot be identified. In particular, even though it is possible to determine a clear abnormal state which is a disorder, there is the problem that it is not possible to determine the human state which includes, a psychological state such as the confusion, uncertainty, irritation, or impatience during the operation of an electronic device; an emotional state such as pleasure/displeasure, or excitement/calmness; and a thinking state such as having nothing in mind, or tackling a mathematical task, or remembering yesterday's dinner, for example.

Consequently, the present invention is conceived in view of the above-described situation, and has as an object to provide a human state estimating device which can estimate, with a high level of accuracy, a human state such as a psychological state, an emotional state, and a thinking state.

Means to Solve the Problems

In order to achieve the aforementioned object, the human state estimating device in an aspect of the present invention is a human state estimating device which estimates a human state which is at least one of a psychological state, an emotional state, and a thinking state, based on fixational eye movement of an eyeball of a user, the human state estimating device includes: a storage unit configured to store reference data in which the human state and a reference profile are corresponded to each other, for each of plural personal attribute information, the personal attribute information indicating at least one of an age bracket, visual acuity, and illness state of a person, the reference profile including a horizontal component which is a left-right direction component of the eyeball in a microsaccade included in normal fixational eye movement of the eyeball in the human state; a video obtaining unit configured to obtain video showing movement of the eyeball including the fixational eye movement of the eyeball of the user, the video being obtained with an eyeball rotation angle accuracy of 0.05 degrees or higher and at a measuring speed of 120 samples per second or higher; an analyzing unit configured to extract the horizontal component of the microsaccade from the fixational eye movement shown in the video, and to generate an actual-measurement profile including the extracted horizontal component; a personal attribute information obtaining unit configured to obtain personal attribute information of the user; and an estimating unit configured to search the reference data stored in the storage unit for a reference profile which corresponds to the personal attribute information obtained by the personal attribute information obtaining unit and which is closest to the actual-measurement profile, and to determine, as the human state estimated for the user, a human state corresponding with the searched-out reference profile. Accordingly, since the human state is estimated using the similarity in personal attributes and using the horizontal component of the microsaccade which has a high dependency on human states, the human state is estimated with a higher accuracy than in with the conventional device which estimates the human state based simply on fixational eye movement.

Here, a "microsaccade" is a fixational eye movement. It is a movement akin to a small jump and is a movement equivalent to a miniature saccade. It should be noted that fixational eye movement includes, aside from a microsaccade, movements called "drift" and "tremor". "Drift" is a small, smooth movement, and a "tremor" is an extremely small, high frequency vibration.

Furthermore, it is preferable that the reference profile includes, as the horizontal component of the microsaccade, a frequency component at a frequency corresponding to a cycle that is typically observed as the microsaccade in a horizontal component of the fixational eye movement, and the analyzing unit is configured to perform frequency analysis of time variation of the horizontal component of the fixational eye movement, and to calculate, as the horizontal component of the microsaccade, the frequency component in a frequency spectrum obtained in the frequency analysis. Accordingly, since a microsaccade is observed at a cycle of 2 to 3 Hz on average, the movement in this frequency band corresponds to the microsaccade, and thus, by making use of this phenomenon, only a microsaccade is extracted reliably and human state estimation accuracy is improved.

Furthermore, the reference profile may further include information regarding at least one of a drift and a tremor which are fixational eye movements, the analyzing unit may be configured to extract information regarding at least one of the drift and the tremor, from the fixational eye movement, and to generate the actual-measurement profile including the extracted information, and the estimating unit may be configured to search for the reference profile that is closest to the actual-measurement profile by referring to the information regarding at least one of the drift and the tremor, in addition to the horizontal component of the microsaccade. Accordingly, human state estimation accuracy can be further improved by estimating the human state using, aside from the microsaccade, various parameters regarding eyeball movement have a dependency on human states.

Furthermore, the analyzing unit may be configured to further analyze, based on the video obtained by the video obtaining unit, eyeball movement including at least one of line of sight, line of sight trajectory, line of sight stationary time, convergence and divergence, fixational eye movement dynamic characteristics, saccade dynamic characteristics, pupil diameter, and pupil dynamic characteristics of the user, and the personal attribute information obtaining unit may have a personal attribute table indicating a correspondence relationship between the eyeball movement and the personal attribute information, and may be configured to identify, by referring to the personal attribute table, personal attribute information corresponding to a result of the analysis of the eyeball movement by the analyzing unit, and to obtain the identified personal attribute information as the personal attribute information of the user. Accordingly, personal attribute information is automatically generated from video used in estimating the human state, and thus the trouble of having the user input personal attribute information is eliminated.

Furthermore, the human state estimating device may further include a registering unit configured to obtain information for identifying the human state of the user, and to register, as new reference data, the obtained information, the personal attribute information obtained by the personal attribute information unit for the user, and the actual-measurement profile generated by the analyzing unit, corresponding to each other. Accordingly, since the reference data used in estimating the human state is registered anew and updated by teaching the user's human state and so on, in advance, human state estimation accuracy can be improved through a learning function.

It should be noted that the present invention can be implemented, not only as such a human state estimating device which estimates a human state by performing eyeball movement measuring, but also as: a human state estimating method; a program causing a computer to execute the steps included in such method; and a computer-readable recording medium, such as a CD-ROM, and so on, on which such program is recorded. For example, by installing such program, as a physical condition evaluation function including an HMI evaluation function or disorders, as an embedded interface in a household appliance, in-vehicle device, and a house, it is possible to perform customized HMI conforming to the state of an individual, or management of an individual's state of health, or early discovery of disorders, and monitoring an illness state, and air conditioning and environmental control.

Effects of the Invention

With the present invention, aside from using the similarity in personal attributes such as a person's age bracket, visual acuity, and illness state, the human state is estimated using the horizontal component of microsaccades which are highly dependent on a human state such as a psychological state, an emotional state, and a thinking state, and thus the human state can be estimated with a higher level of accuracy than with the conventional device which estimates the human state based simply on fixational eye movement.

BRIEF DESCRIPTION OF DRAWINGS

FIG. 4 is a diagram showing the data structure of human state information.

FIG. 9 is a flowchart showing the operation regarding estimation of a human state performed by the human state estimating device.

FIG. 16 is a diagram for describing the correlation between mental state and microsaccades; (a) is a diagram showing measuring conditions for a target, and (b) is a diagram showing normal fixational eye movement when no orders are given to a subject, and (c) is a diagram showing the trajectory of small eye movement when the subject is counting prime numbers.

NUMERICAL REFERENCES

Figure 1:
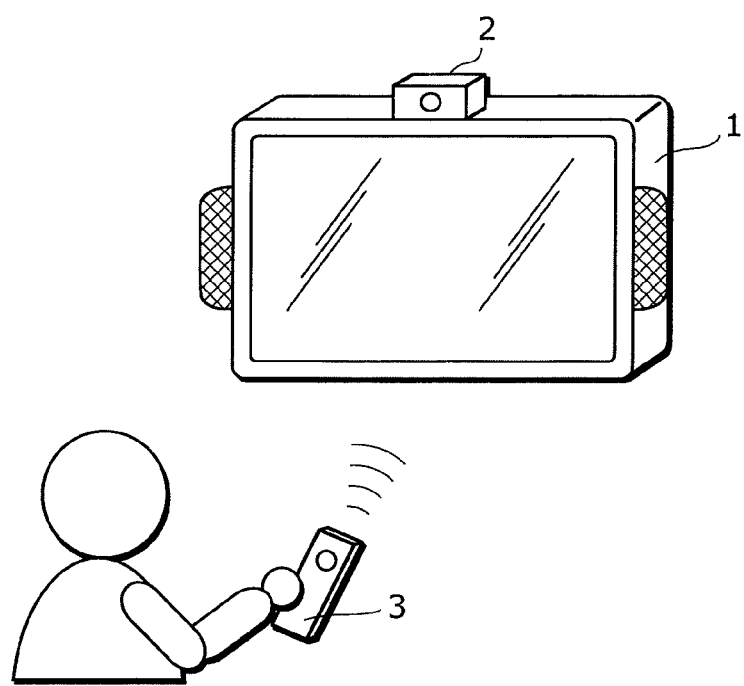
FIG. 1 is a diagram showing an example of an application of a human state estimating device in the present invention.

1 Digital television
2 Camera
3 Remote control
10 Human state estimating device
11 Video obtaining unit
12 Analyzing unit
12a Image clipping unit
12b Eyeball movement analyzing unit
13 Personal attribute information obtaining unit
13a Personal attribute table
14 Input unit
15 Estimating unit
16 Storing unit
17 Reference data
17a Personal attribute information
17 Human state information
17c Reference profile
18 Registering unit
19 Display unit
20 Eyeball image sorting control unit
21 Sclera image analyzing unit
22 Cornea image analyzing unit
32 Wide angle camera
33 High-magnification lens
38 High-speed camera

DETAILED DESCRIPTION OF THE INVENTION

Hereinafter, an embodiment of the present invention shall be described in detail with reference to the Drawings.

FIG. 1 is a diagram showing an example of an application of the human state estimating device in the present invention. The human state estimating device in the present invention is a device which obtains video including an eyeball of a user (here, an operator of a digital television 1) using a camera 2 provided on an upper portion of the digital television 1, analyzes the fixational eye movement of the user's eyeball from the video, and estimates, based on the analysis result, a human state which is at least one of a psychological state, an emotional state, and a thinking state of the user. The human state estimating device is built into the camera 2 or the digital television 1. The digital television 1 provides, to the user operating a remote control, an operating menu conforming to the human state estimated by the human state estimating device. For example, the digital television 1 provides a more detailed operating menu to a user estimated as being confused.

Figure 2:
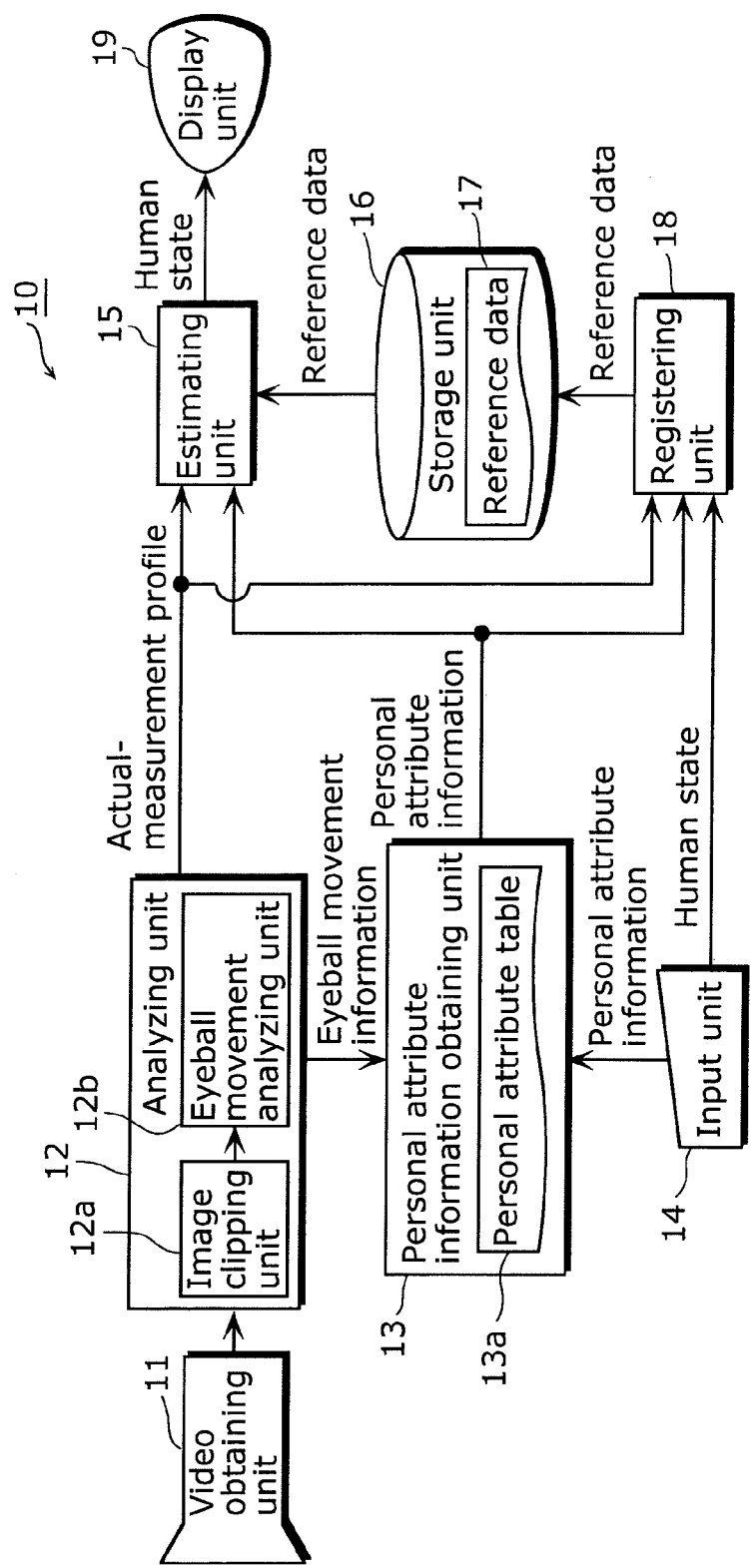
FIG. 2 is a function block diagram showing the configuration of a human state estimating device in an embodiment of the present invention.

FIG. 2 is a block diagram showing the functional configuration of a human state estimating device 10 in the present invention. As shown in the figure, the human state estimating device 10 is a device which estimates a human state, which is at least one of a psychological state, an emotional state, and a thinking state, based on fixational eye movement of an eyeball of a user, and includes a video obtaining unit 11, an analyzing unit 12, a personal attribute information obtaining unit 13, an input unit 14, an estimating unit 15, a storage unit 16, a registering unit 18, and a display unit 19.

The video obtaining unit 11 is a video camera which obtains video showing eyeball movement including the fixational eye movement of the user, with an eyeball rotation angle accuracy of 0.05 degrees or higher, and a measuring speed of 120 samples per second or higher. The video obtaining unit 11 includes not only an ultraviolet-visible camera, but also an infrared (or near-infrared) camera.

It should be noted that 0.05 degrees is the minimum eyeball rotation angle accuracy (maximum allowable error) required for reliably detecting fixational eye movement, and is a value (10 μm/12 mm (average radius of a human eyeball)×180/n) obtained by converting 10 μm of eyeball surface into an eyeball rotation angle. Here, 10 μm of an eyeball surface is assumed as the minimum accuracy because, since the minimum vibration amplitude during a drift in fixational eye movement is defined to be 20 μm ("Gankyuundo no Jikkenshinrigaku (Experimental Psychology of Eye Movement)" by Ryoji Imosaka, Sachio Nakamizo, Koga Kazuo; Nagoya University Press: Non Patent Reference 1), a drift and a microsaccade, which shows a greater swing than a drift, can be detected, among fixational eye movements, by detecting the movement distance of an arbitrary point on the eyeball surface at half of such accuracy.

In addition, upon actual measurement of the fixational eye movement of an eyeball by the inventors, it has been determined through experiments that the vibration amplitude in a small microsaccade is about 0.1 degree. As such, in order to reliably measure such type of microsaccade, a resolution capability of half of such vibration amplitude, that is 0.05, is necessary.

Furthermore, since the movement speed of a microsaccade is 50 to 100 Hz (see aforementioned Non Patent Reference 1), a measuring speed of 120 samples per second or more is assumed in order to reliably detect a microsaccade by sampling images at a frame rate exceeding such movement speed.

In addition, upon actual measurement of the fixational eye movement of an eyeball by the inventors, it has been determined through experiments that the reciprocation time of a small microsaccade is more or less 25 ms. In order to reliably detect such type of microsaccade, it is necessary to set the sampling cycle at or below ⅓ of the reciprocation time of such type of microsaccade, that is 25/3=8.3 ms or less. Therefore, in order to reliably detect a small microsaccade, the number of samples per second needs to be 120 or more.

The analyzing unit 12 is a processing unit that is implemented through a CPU, a memory, a program, and the like, for generating an actual-measurement profile indicating the user's eyeball movements, by performing image processing on the video obtained by the video obtaining unit 11. The analyzing unit 12 includes an image clipping unit 12a and an eyeball movement analyzing unit 12b.

The image clipping unit 12a clips out images of the user's face by performing contour processing, and so on, on each picture making up the video sent from the video obtaining unit 11.

The eyeball movement analyzing unit 12b analyzes the eyeball movements (user's line of sight, line of sight trajectory, line of sight stationary time, convergence/divergence, eye-blink rate, blinking dynamic characteristics (time required to close an eyelid/time required to open the eyelid), pupil diameter, pupil dynamic characteristics (rate of change of the pupil diameter when a change in the amount of light is detected, and frequency analysis pattern characteristics of the rate of change), saccade dynamic characteristics (movement speed or corrective saccades, or variations in the horizontal direction and vertical direction, vibration amplitude, and so on), and fixational eye movement dynamic characteristics (fixational eye movement trajectory, small-movement speed, small-movement frequency analysis pattern, swing characteristics, and so on)) in the face images clipped out by the image clipping unit 12*a*.

For example, the image clipping unit 12*a* analyzes the dynamic characteristics of the fixational eye movement (microsaccade, drift, and tremor) by obtaining the movement trajectory of the line of sight from the face image, identifies the pupil diameter by recognizing a pupil image with respect to the face image, and sends information (values of eyeball movement parameters) indicating the respective analysis results as an actual-measurement profile, to the estimating unit 15 and the registering unit 18. Furthermore, the eyeball movement analyzing unit 12*b* identifies the position and size of the pupil for the face image clipped out by the image clipping unit 12*a*, based on a prior setting, and calculates the time variation thereof, and to thereby analyzing the eyeball movement including the user's line of sight, line of sight trajectory, line of sight stationary time, convergence and divergence, the fixational eye movement dynamic characteristics, saccade dynamic characteristics, pupil diameter and pupil dynamic characteristics, and sends eyeball movement information indicating the results of the analysis to the personal attribute information obtaining unit 13.

The personal attribute information obtaining unit 13 is a processing unit that is implemented through a CPU, a memory, a program, and the like, which obtains personal attribute information indicating at least one out of the user's age bracket, visual acuity, and illness state, as information for increasing the human state estimating accuracy by the human state estimating device 10, and sends the obtained personal attribute information to the estimating unit 15 and the registering unit 18. Specifically, the personal attribute information obtaining unit 13 includes a personal attribute table 13*a* indicating the relationship between eyeball movement and personal attribute information, and, by referring to the personal attribute table 13*a* when eyeball movement information is sent from the analyzing unit 12, identifies a personal attribute information corresponding to the eyeball movement information sent from the analyzing unit 12, and obtains the identified personal attribute information as the personal attribute information of the user. On the other hand, when eyeball movement information is not sent from the analyzing unit 12, the personal attribute information obtaining unit 13 obtains personal attribute information by obtaining information regarding the user's age bracket, visual acuity, and illness state, from the user via the input unit 14.

Figure 3:
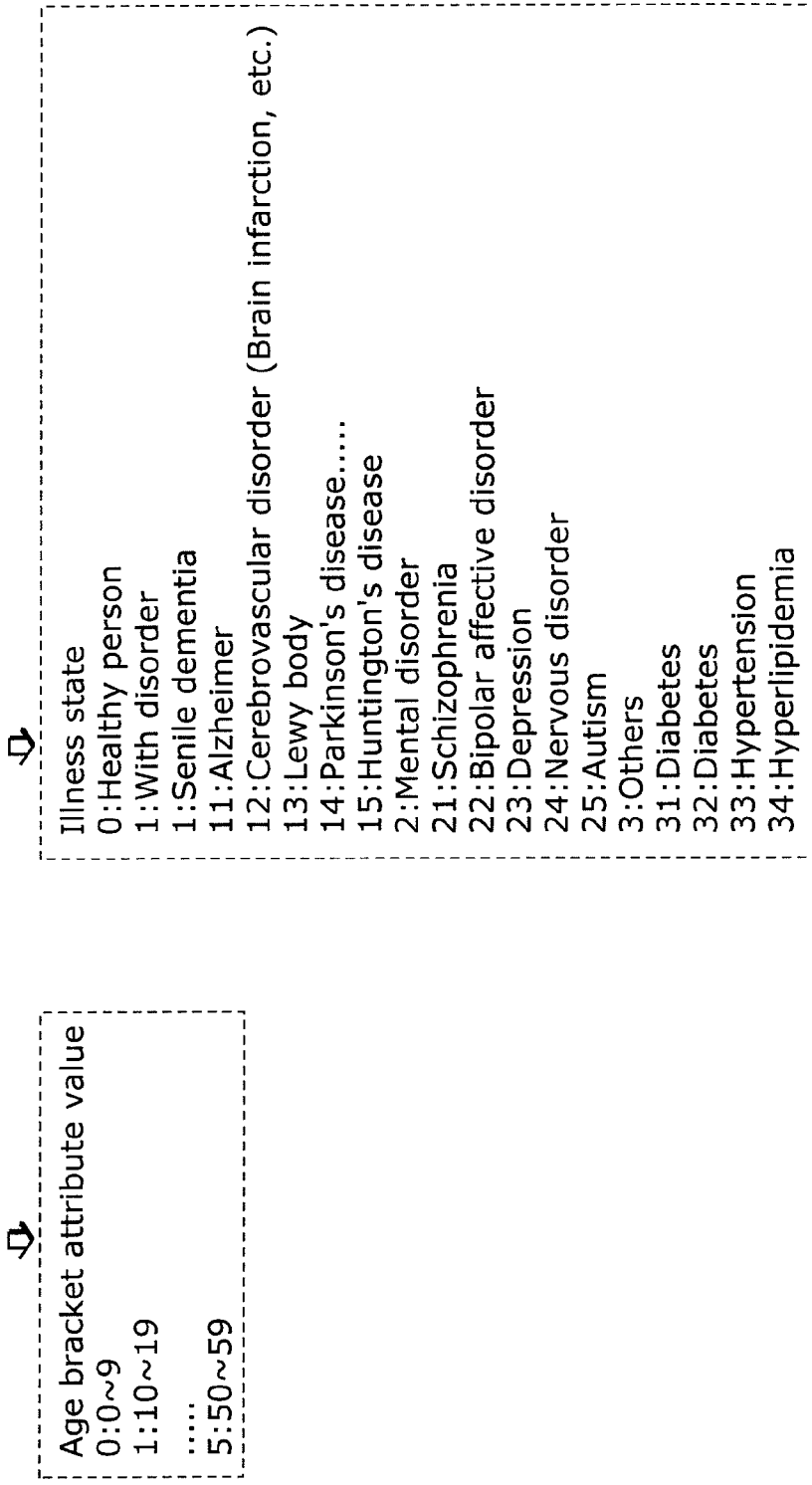
FIG. 3 is a diagram showing the data structure of personal attribute information.

FIG. 3 is a diagram showing the data structure of personal attribute information. The personal attribute information is made up of: a field storing an "age bracket attribute value" identifying the range of the age bracket; a field storing visual acuity, such as 1.0 and so on; and a field storing a number identifying any of the illustrated states of illness. It should be noted that values denoting unknown, a standard value (default value), and so on, may be stored in each field.

The input unit 14 is an operation button, a keyboard, a mouse, or the like for the inputting of personal attribute information or a human state by the user, and corresponds to a remote control 3 in FIG. 1. The input unit 14 outputs personal attribute information to the personal attribute information obtaining unit 13, and outputs information identifying a human state (human state information) to the registering unit 18.

FIG. 4 is a diagram showing the data structure of human state information. The human state information is made up of a field storing a number identifying at least one psychological state such as composure, uncertainty, confusion, and so on; a field storing a number identifying at least one emotional state such as a degree of pleasure/displeasure, a level of excitement/calmness, a level of nervousness/relaxation; and a field storing a number identifying at least one thinking state such as a state in which a mathematical problem has been given, a state in which a memory task has been given, a state in which a thinking task has been given, and so on.

The storage unit 16 is a storage device such as a memory or a hard disk which stores reference data 17 in which a human state and a reference profile, which is information regarding standard eyeball movement in the human state, are corresponded to each other, for each of plural personal attribute information. Here, the reference profile includes: information indicating a horizontal component of a microsaccade (an eyeball's left-right directional component) (more specifically, a frequency component at a frequency corresponding to a cycle which is typically observed as a microsaccade in a horizontal component of fixational eye movement); information regarding drift and tremor; information regarding pupil diameter; and so on.

Figure 5:
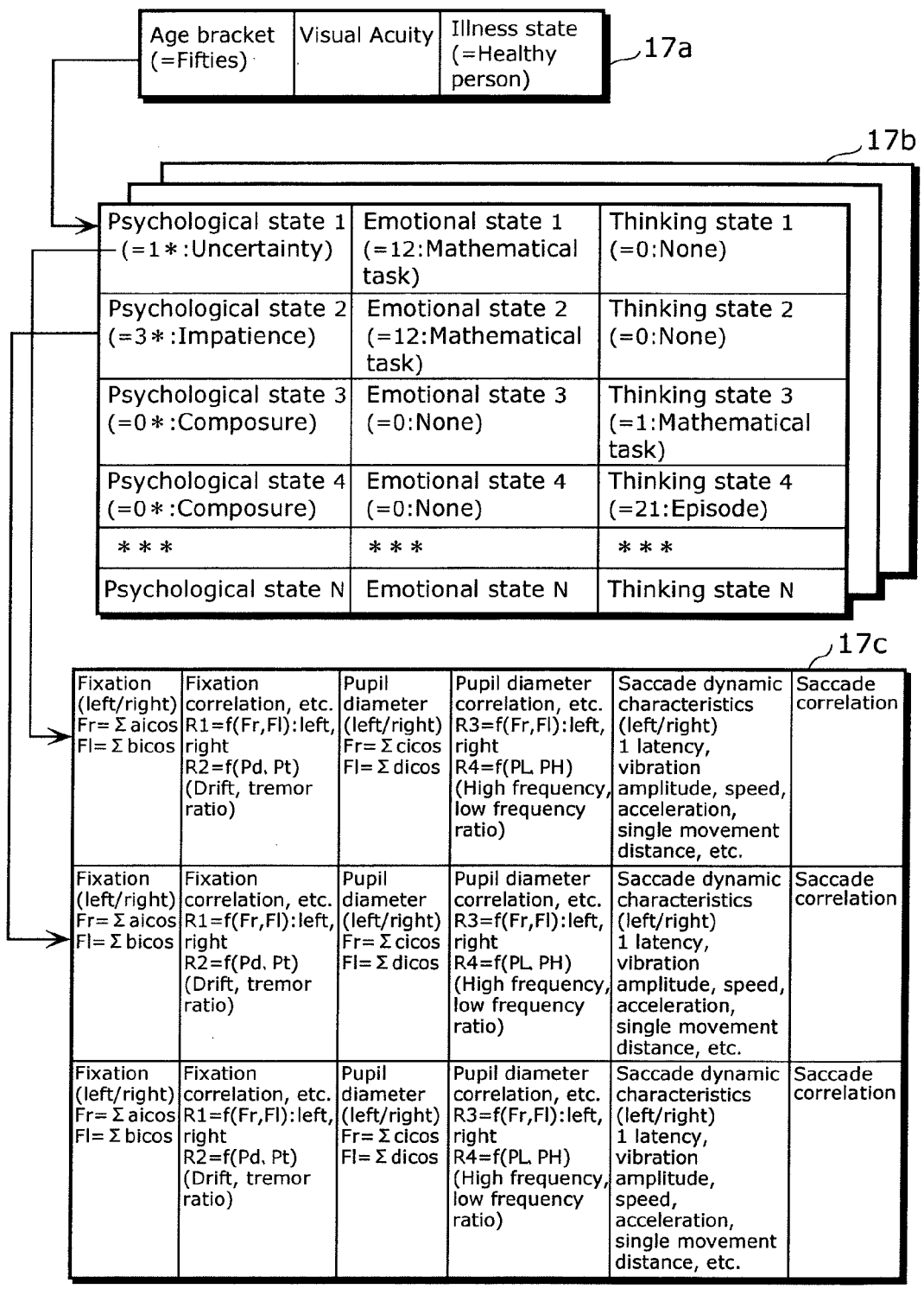
FIG. 5 is a diagram showing the data structure of reference data.

FIG. 5 is a diagram showing the data structure of the reference data 17. The reference data 17 is data in which the correspondence relationship between human state information 17*b* and reference profile 17*c* are registered for each of different plural personal attribute information 17*a*. Here, the reference profile 17*c* is a collection of pre-registered eyeball movement parameters, corresponding to a human state information 17*b*. FIG. 5 shows the correspondence relationship between human state information 17*b* and reference profile 17*c* that are registered for one out of the plural personal attribute information 17*a*. Here, for a person having a personal attribute in which the age bracket indicates the fifties, visual acuity indicates the complete range, and the illness state indicates a healthy person (personal attribute information 17*a*), a typical value is stored for every value of the eyeball movement parameters in the case of a human state of "a psychological state indicating uncertainty, an emotional state indicating displeasure, and a thinking state indicating none" (human state information 17*b*). For example, the values for the horizontal component of the microsaccade ("fixation (left/right)" in reference profile 17*c*), the values for information regarding drift and tremor ("fixation (left/right)" in reference profile 17*c*, the values for information regarding pupil diameter ("pupil diameter (left/right)" in reference profile 17*c*), and so on are stored.

The estimating unit 15 is a processing unit that is implemented through a CPU, a memory, a program, and the like, which: searches the reference data 17 stored in the storage unit 16 for a reference profile which corresponds to the personal attribute information sent from the personal attribute information obtaining unit 13 and which is closest to the actual-measurement profile sent from the analyzing unit 12; determines the human state corresponding to the searched-out reference profile, as the human profile estimated for the user; and notifies information indicating the determined human state to the display unit 19.

The display unit 19 is a Liquid Crystal Display (LCD), a Plasma Display Panel (PDP), an organic Electro Luminescent (EL) display, a CRT, or the like, which displays the human state information sent from the estimating unit 15, and displays an operating menu to the user, and corresponds to the display screen of the digital television 1 in FIG. 1.

The registering unit 18 is a processing unit that is implemented through a CPU, a memory, a program, or the like, which obtains, via the input unit 14, information for identifying the user's human state, and registers, as new reference data 17 in the storage unit 16, the obtained information, the personal attribute information sent from the personal attribute information obtaining unit 13 and the actual-measurement profile sent from the analyzing unit 12 with regard to the user, corresponding to each other. With this, aside from being able to estimate the human state, the human state estimating device 10 is capable of learning through adding and updating data (reference data 17) which becomes the reference for the estimation.

Here, the details of the eyeball movement analysis by the eyeball movement analyzing unit 12b, and the significance of analyzing the eyeball movement shall be described.

Figure 6:
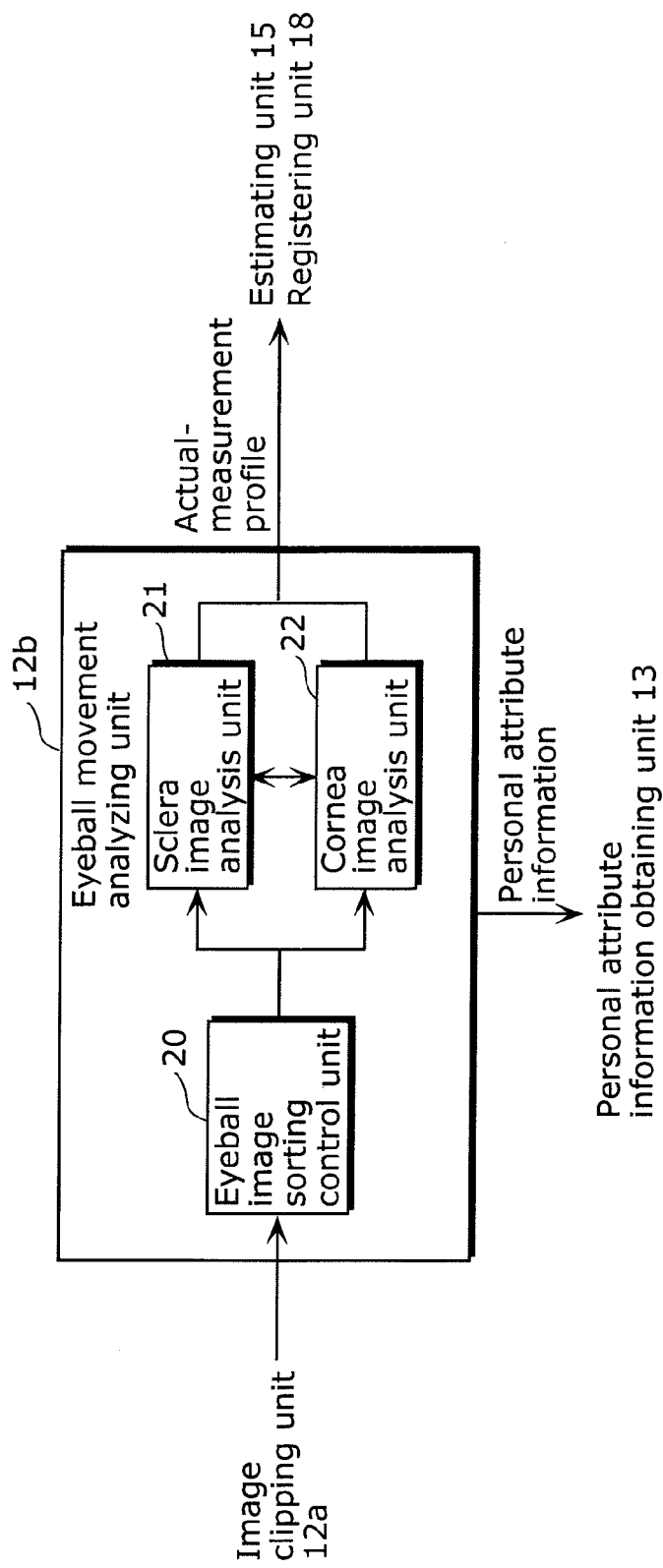
FIG. 6 is a function block diagram showing the detailed configuration of an eyeball movement analyzing unit in FIG. 2.

FIG. 6 is a function block diagram showing the detailed configuration of the eyeball movement analyzing unit 12b shown in FIG. 2. The eyeball movement analyzing unit 12b includes an eyeball image sorting control unit 20, a sclera image analyzing unit 21, and a cornea image analyzing unit 22.

The eyeball image sorting control unit 20 detects the change in image contrast, color hue, and so on, and sorts the sclera (white part of the eye) and the cornea (black part of the eye) images from within the face images clipped out by the image clipping unit 12a, and outputs information regarding the sclera image to the sclera image analyzing unit 21, and outputs information regarding the cornea image to the cornea image analyzing unit 22. The sclera image analyzing unit 21 analyzes the dynamic characteristics of the fixational eye movement by DP (Dynamic Programming) matching of scleral vascular patterns. The cornea image analyzing unit 22 calculates the static characteristics (position, size, and so on) and the dynamic characteristics (time variation of the position, size, and so on) of the cornea, by extracting the images of the iris and pupil through contour extraction and so on, and analyzing the extracted images. The result of the analysis by the sclera image analyzing unit 21 and the cornea image analyzing unit 22 are sent to the estimating unit 15 and the registering unit 18 as an actual-measurement profile indicating the user's eyeball movement, and sent to the personal attribute information obtaining unit 13 as eyeball movement information for automatically generating personal attribute information. It should be noted that, in the case where only the sclera image is used in the eyeball movement analysis, the cornea image analyzing unit 22 need not be included in the configuration.

Figure 7A:
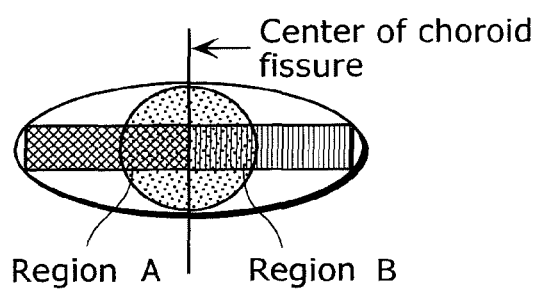
FIG. 7 is a diagram for describing a method for measuring line of sight in the horizontal direction.
Figure 7B:
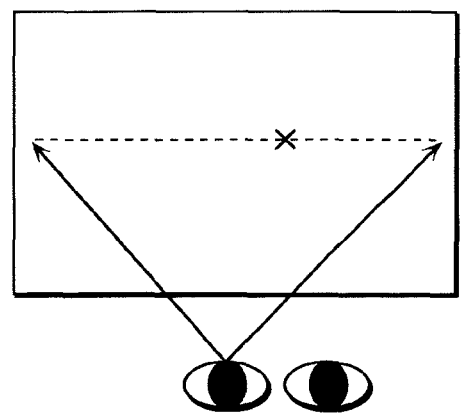
Figure 8A:
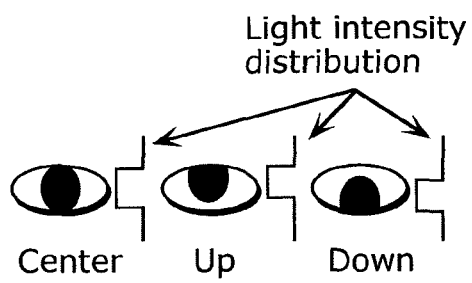
FIG. 8 is a diagram for describing a method for measuring line of sight in the vertical direction.
Figure 8B:
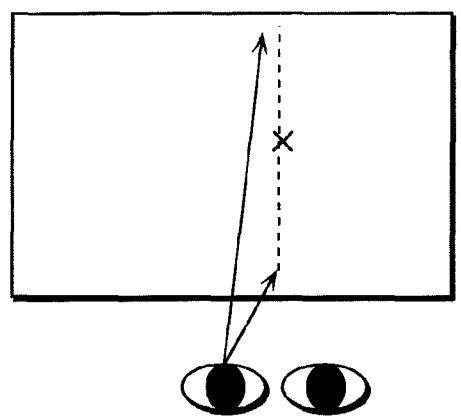

Furthermore, in the eyeball movement analyzing unit 12b, the analysis of the line of sight from the face image clipped out by the image clipping unit 12a is performed by the sclera image analyzing unit 21 and the cornea image analyzing unit 22. As an analyzing method, as shown in FIG. 7 and FIG. 8, the point on the display unit 19 (screen) at which the user gazes is identified according to the positional relationship and ratio between the sclera and the cornea in the horizontal direction and the vertical direction. FIG. 7 is a diagram describing a method for measuring the line of sight in the horizontal direction. Here, the appearance of the identification of the horizontal direction of the line of sight, according the positional relationship and ratio between the sclera and the cornea in the horizontal direction is illustrated. Furthermore, FIG. 8 is a diagram describing a method for measuring the line of sight in the vertical direction. Here, the appearance of the identification of the vertical direction of the line of sight, according to the positional relationship and ratio between the sclera and the cornea in the vertical direction is illustrated.

Although, normally, the line of sight can be detected using only the eyeball movement information of the horizontal direction and the vertical direction, since depth cannot be detected, the convergence (the esotropial state when looking up close) or divergence (the exotropial state when looking far) of the left and right eyes is further detected from the eyeball movement information, and a three-dimensional fixation point is extracted. In order to further increase accuracy, convergence/divergence may be detected by measuring beforehand the degree of esotropia/exotropia when gazing at the display unit 19 through pre-calibration.

In the present embodiment, when the human state estimating device 10 is activated, the video obtaining unit 11 begins the imaging of the face of the user. During operation of the human state estimating device 10, every minute for example, the video of the user for the immediately preceding 1 minute is analyzed, the psychological state, the emotional state, or the thinking state is estimated, and the estimated human state is outputted to the display unit 19. In addition, it is possible to change the display state of the screen, and change the device control method in accordance with such human state. Specifically, the human state estimating device 10 changes, every minute for example, the display state of the screen in accordance with the user's human state. In addition, the video obtaining unit 11 begins the imaging of the face of the user. The imaged video data is accumulated in a buffer memory not shown in the figures. Here, for example, in the aforementioned video taken in near-infrared light, since the reflection rate for the iris is high, only the pupil is dark and the iris is of a brightness that is slightly darker than the white of the eye. Specifically, in video taken in near-infrared light, the pupil is the brightest, followed sequentially by the iris, the white of the eye, and skin such as the eyelid. As such, by making use of such difference in brightness, it is possible to distinguish the pupil, eyelid, and so on.

Furthermore, the user's physiological/psychological state can also be estimated through the variation in the pupil diameter. The pupil constricts when light enters the eye (called light reaction), and dilates in the dark. With a younger person, pupil diameter changes from a minimum diameter of about 2 mm to a maximum of about 8 mm. In contrast, with the elderly, the pupil diameter does not dilate as much as with a younger person even in the dark, and the maximum diameter is about 6 mm. Furthermore, even with regard to light reaction, response speed characteristics are different between a younger person and the elderly, and an elderly person has a slower reaction.

The following applies to the change in pupil diameter. Even when the amount of light entering the eye is constant, the size of the pupil fluctuates in a low frequency. In addition, during a tense moment, the pupil dilates significantly (mydriasis), and quivering is also unnoticeable. However, when feeling fatigue or drowsiness, the pupil constricts (myosis) and begins to quiver. In addition, the pupil dilates with the level of fatigue or drowsiness. Furthermore, the pupil dilates when looking at something of interest. In contrast, the size of the pupil hardly changes with respect to something that is of little interest such as a boring photograph, a hard-to-understand abstract painting, or the like. In this manner, the change in the pupil reflects the psychological state of a person. As such, by measuring the pupil diameter, pupil reaction, or the like, it is possible to estimate the user's age bracket or degree of interest regarding an object, and psychological state, and so on.

Furthermore, in order to improve the accuracy of human state estimation using eyeball movement measurement, which is easily influenced by age, visual acuity, or illness state, in the present embodiment, the personal attribute information shown in FIG. 3 is generated by the personal attribute information obtaining unit 13 and sent to the estimating unit 15. The estimating unit 15 narrows down the search object for the reference data 17 stored in the storage unit 16 by limiting the search to information belonging to personal attribute information that is identical or similar to the inputted personal attribute information. Specifically, although the estimating unit 15 searches within the reference data 17 for reference profile 17c which is closest to the actual-measurement profile including the eyeball movement information sent from the eyeball movement analyzing unit 12b, at this time, the estimating unit 15 searches by limiting the search to the reference profile 17c belonging to the personal attribute information 17a which is identical or similar to the personal attribute information sent from the personal attribute information obtaining unit 13, and sends the human state information 17b corresponding to the searched-out reference profile 17c to the display unit 19, as the human state of the user.

It should be noted that since the eyeball movement is analyzed every minute in the present embodiment, transmission amount may be reduced by sending the human state information, and so on, to the display unit 19 only when the previously estimated human state and the currently estimated human state are different. Furthermore, the details of the personal attribute information shown in FIG. 3 may be defined, in an initial state, with defaults such as age bracket=undetermined, visual acuity=undetermined, illness state=undetermined. Furthermore, since it is possible to determine the age bracket of the user by measuring the pupil diameter, pupil reaction, or the like, inputting the age bracket becomes unnecessary.

Furthermore, since the sclera image analyzing unit 21 in the present embodiment analyzes the dynamic characteristics of the fixational eye movement through DP matching of scleral vascular patterns, person authentication by epibulbar vascular patterns becomes possible in the same manner as person authentication by venous pattern matching, and by previously corresponding the result of the person authentication and personal attribute information prepared in advance to each other, and estimating the human state using personal attribute information corresponding to the authentication result, it becomes unnecessary to generate personal attribute information every time and estimation accuracy is improved.

Furthermore, although the variation of pupil diameter, including factors such as age, and so on, is different from person to person, iris information that allows extremely accurate authentication through person authentication and so on can be obtained using the video signal from the same camera (video obtaining unit 11), and thus, by building an iris authentication mechanism into the eyeball movement analyzing unit 12b, more accurate estimation of the physiological/psychological state, which takes into consideration personal variation rate, is possible.

Next, the operation of the human state estimating device 10 in the present embodiment, configured in the aforementioned manner shall be described.

FIG. 9 is a flowchart showing the operation regarding the estimation of a human state performed by the human state estimating device 10 in the present embodiment.

First, the video obtaining unit 11 obtains video showing eyeball movement including the fixational eye movement of the user, with an eyeball rotation angle accuracy of 0.05 degrees or higher, and a measuring speed of 120 samples per second or higher (S10).

Next, the image clipping unit 12a of the analyzing unit 12 clips out images of the user's face by performing contour processing, and so on, on each picture making up the video sent from a wide-angle camera 32 of the video obtaining unit 11 (S20).

Subsequently, the eyeball movement analyzing unit 12b of the analyzing unit 12 analyzes the dynamic characteristics of the fixational eye movement (microsaccades, drifts, and tremors) by obtaining the movement trajectory of the line of sight for the face image clipped out by the image clipping unit 12a, and identifies the pupil diameter by recognizing the image of the pupil with respect to the face image (S12). More specifically, as information regarding microsaccades, the eyeball movement analyzing unit 12b separates the data indicating fixational eye movement into the horizontal component (eyeball's left-right directional component) and the vertical component (eyeball's up-down directional component), performs frequency analysis by performing a Fourier series expansion on the separated horizontal component, and generates, as an actual-measurement profile including the horizontal component of the microsaccade, a frequency component at a frequency (2 to 3 Hz) corresponding to the cycle which is typically observed as a microsaccade in the obtained frequency spectrum. Furthermore, the eyeball movement analyzing unit 12b likewise calculates the frequency component corresponding to the movement speed of the drift and the tremor, out of the data indicating the fixational eye movement so as to generate an actual-measurement profile for drifts and tremors.

Meanwhile, the personal attribute information obtaining unit 13 obtains personal attribute information indicating at least one out of the user's age bracket, visual acuity, and illness state, as information for increasing the human state estimating accuracy by the human state estimating device 10 (S13).

Subsequently, the estimating unit 15 searches for a reference profile which corresponds to the personal attribute information sent from the personal attribute information obtaining unit 13 and which is closest to the actual-measurement profile sent from the analyzing unit 12 (S15), by referring to the reference data 17 stored in the storage unit 16 (S14), and determines the human state corresponding to the searched-out reference profile, as the human profile estimated for the user (S16). More specifically, the estimating unit 15 identifies, from within the reference data 17, personal attribute information 17a which matches or is closest to the personal attribute information sent from the personal attribute information obtaining unit 13, and reads, from the reference data 17, the correspondence relationship (FIG. 5) between the human state information 17b and the reference profile 17c that are registered with regard to the identified personal attribute information 17a. Subsequently, by referring to the data of the correspondence relationship that has been read out, the estimating unit 15 calculates the degree of coincidence between the actual-measurement profile and the reference profile for the eyeball movement parameters such as the horizontal component of the microsaccade, information regarding drift and tremor, and information regarding pupil diameter, and so on (for example, the ratio of the value of the reference profile and the value of the actual-measurement profile, for each eyeball movement parameter), identify the reference profile 17c having the highest total value for such degrees of coincidence, and notifies the human state information 17b corresponding to the identified reference profile 17c, as information indicating the human state of the user, to the display unit 19.

It should be noted that, in the personal attribute information sent from the personal attribute information obtaining unit 13, all of the age bracket, visual acuity, and state of affection are not necessarily filled up with definitive values. For example, in the case of personal attribute information defined only with age bracket=fifties, the estimating unit 15: interprets this as personal attribute information denoting the user's age bracket=fifties, visual acuity=default (not pertinent), state of affection=default (=healthy person); searches for a reference profile 17*c* that is closest to the actual-measurement profile, from within the reference profiles 17*c* belonging to the personal attribute information 17*a* that is the same as the aforementioned personal attribute information; and estimates that the human state information 17*b* corresponding to the searched-out reference profile 17*c* is the human state of the user.

Finally, the display unit 19 displays the human state information sent from the estimating unit 15 (S17).

In this manner, the human state of the user is estimated by the human state estimating device 10 in the present embodiment. According to the human state estimating device 10, the human state is estimated accurately compared to the conventional estimation of the human state based simply on eyeball movement (or fixational eye movement) since (1) the human state is estimated based on the fixational eye movement, particularly the horizontal component of the microsaccade which has a high correlation with the human state, from the video obtained by the high-performance video obtaining unit 11, and (2) the human state is estimated by making use of the similarity of personal attributes, in addition to the eyeball movement.

Figure 10:
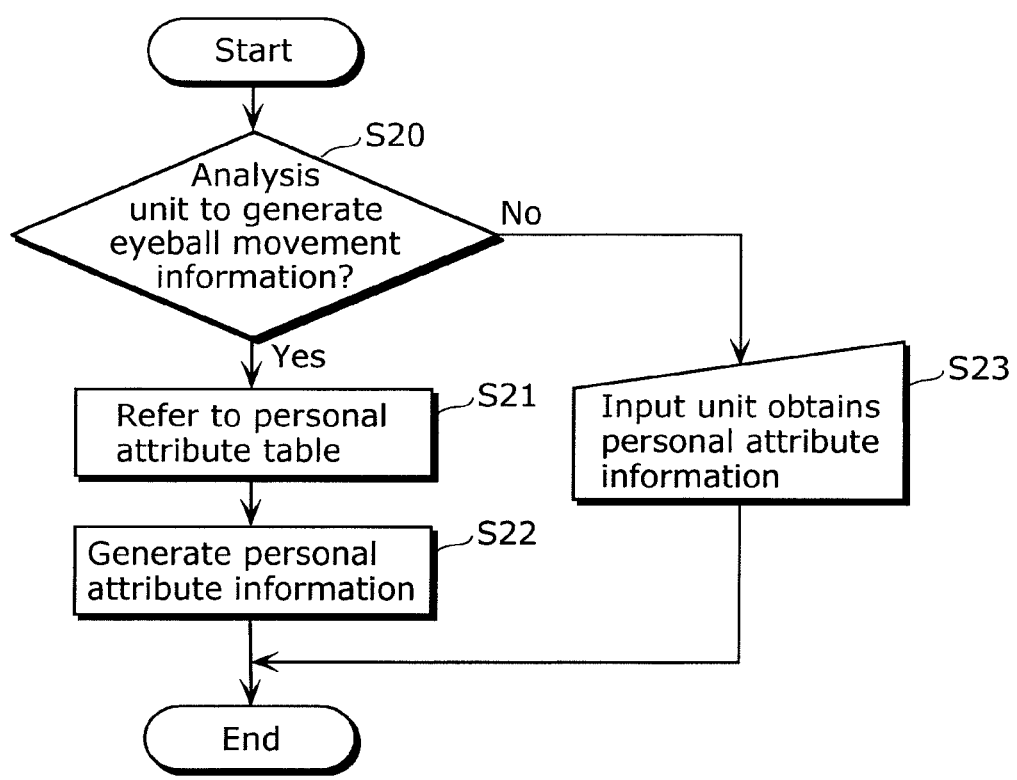
FIG. 10 is a flowchart showing the operation regarding automatic generation of personal attribute information performed by the human state estimating device.

FIG. 10 is a flowchart showing the operation regarding the automatic generation of personal attribute information performed by the human state estimating device 10 in the present embodiment.

First, the personal attribute information obtaining unit 13 judges whether or not eyeball movement information will be sent from the analyzing unit 12 (S20). It should be noted that, in the analyzing unit 12, whether or not eyeball movement information is to be generated by the eyeball movement analyzing unit 12*b* is determined through a prior setting by the user, and when eyeball movement information is generated by the eyeball movement analyzing unit 12*b*, such eyeball movement information is transmitted from the analyzing unit 12 to the personal attribute information obtaining unit 13.

As a result, when eyeball movement information is to be sent from the analyzing unit 12 (Yes in S20), the personal attribute information obtaining unit 13, by referring to the personal attribute table 13*a* (S21), identifies the personal attribute information corresponding to the eyeball movement information sent from the analyzing unit 12, and generates the identified personal attribute information as the personal attribute information of the user (S22). On the other hand, when eyeball movement information will not be sent from the analyzing unit 12 (No in S20), the personal attribute information obtaining unit 13 obtains personal attribute information by obtaining information regarding the user's age bracket, visual acuity, and illness state, from the user via the input unit 14 (S23).

In this manner, according to the human state estimating device 10 in the present embodiment, personal attribute information is automatically generated by making use of video obtained by the video obtaining unit 11, that is, the video obtained for estimating the human state. In addition, the automatically generated personal attribute information is used in the estimating of the human state, together with the actual-measurement profile generated by the analyzing unit 12. Therefore, according to the human state estimating device 10, estimation of the human state with high accuracy can be implemented without needing special operations in order to obtain personal attribute information.

Figure 11:
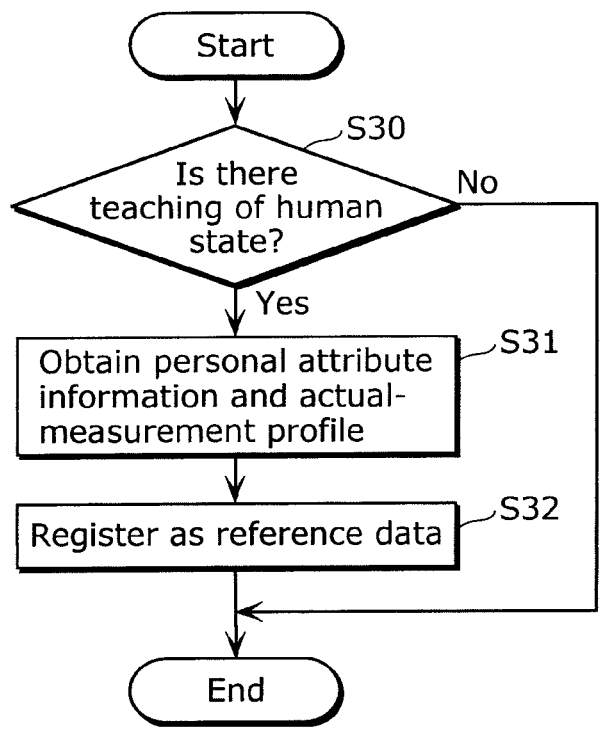
FIG. 11 is a flowchart showing the operation regarding registration of reference data performed by the human state estimating device.

FIG. 11 is a flowchart showing the operation regarding the registration of reference data 17, performed by the human state estimating device 10 in the present embodiment.

First, the registering unit 18 judges whether or not information for identifying the human state of the user has been inputted from the input unit 14, that is, whether or not there is a teaching of the human state (S30). It should be noted that the operating mode of the human state estimating device 10 is determined to be either a "human state estimating mode" or a "reference data registering mode", according to a prior setting by the user. In addition, when the human state estimating device 10 is in the "reference data registering mode", the registering unit 18 determines that there is a teaching of the human state.

As a result, only in the case where there is a teaching of the human state (Yes in S30), the registration unit 18 receives the personal attribute information of the user from the personal attribute information obtaining unit 13, and receives the actual-measurement profile of the user from the analyzing unit 12 (S31), and registers these and the human state currently inputted from the input unit 14 corresponding to each other (assuming the actual-measurement profile to be the reference profile), as new reference data 17, in the storage unit 16 (S32).

With this, aside from being able to estimate the human state, the human state estimating device 10 in the present embodiment is capable of learning through adding and updating data (reference data 17) which becomes the reference for the estimation.

As described above, in the human state estimating device 10 in the present embodiment, the personal attribute information obtaining unit 13 generates personal attribute information based on the eyeball movement information sent from the analyzing unit 12 or the input from the input unit 14. In addition, the personal attribute information generated through either case is used as supplementary information for estimating the human state in the estimating unit 15. Therefore, according to the human state estimating device 10, even when the analyzing unit 12 is of an inexpensive type which does not include a function for generating eyeball movement information to be sent to the personal attribute information obtaining unit 13, personal attribute information corresponding to personal attributes (and including default values when necessary) is generated by simple inputs, such as the age bracket and so on, by the user, and the generated personal attribute information is used in estimating the human state, and thus accurate human state estimation is implemented.

Furthermore, by pre-defining all personal attribute information as default or self-reported values initially, and performing human state estimation based only on the measured eyeball movement and outputting the result to the display unit 19, it is also possible to consider the possibility of yet unexposed disorders or to consider the possibility of dishonest self-reporting, when there is a deviation in the self-report or diagnosis result and the details displayed on the display unit 19.

In addition, in the case where for example the change in the currently measured pupil diameter frequently exceeds 8 mm, or the variation speed of the pupil diameter is as fast as with a 20 year old when processing is carried out with a default age bracket of 50 years old, the "age bracket" of the personal attribute information may be changed dynamically.

It should be noted that since the eyeball movement is analyzed every minute in the present embodiment, transmission amount may be reduced by having the estimating unit 15 send the human state information to the display unit 19 only when the previously estimated human state and the currently estimated human state are different. Furthermore, it is also possible to have a mechanism in which, the details of the personal attribute information shown in FIG. 3 are pre-defined, in an initial state, with defaults such as age bracket=undetermined, visual acuity=undetermined, illness state=undetermined, and accuracy is enhanced by updating only the defaults when there has been an input from the input unit 14 or an automatic analysis by the personal attribute information obtaining unit 13. Furthermore, since it is possible to determine the age bracket of the user by measuring the pupil diameter, pupil reaction, or the like, it becomes unnecessary to input the age bracket.

Next, the significance of using information regarding fixational eye movement, particularly microsaccades, in order for the human state estimating device 10 in the present invention to estimate a human state shall be described.

Figure 12A:
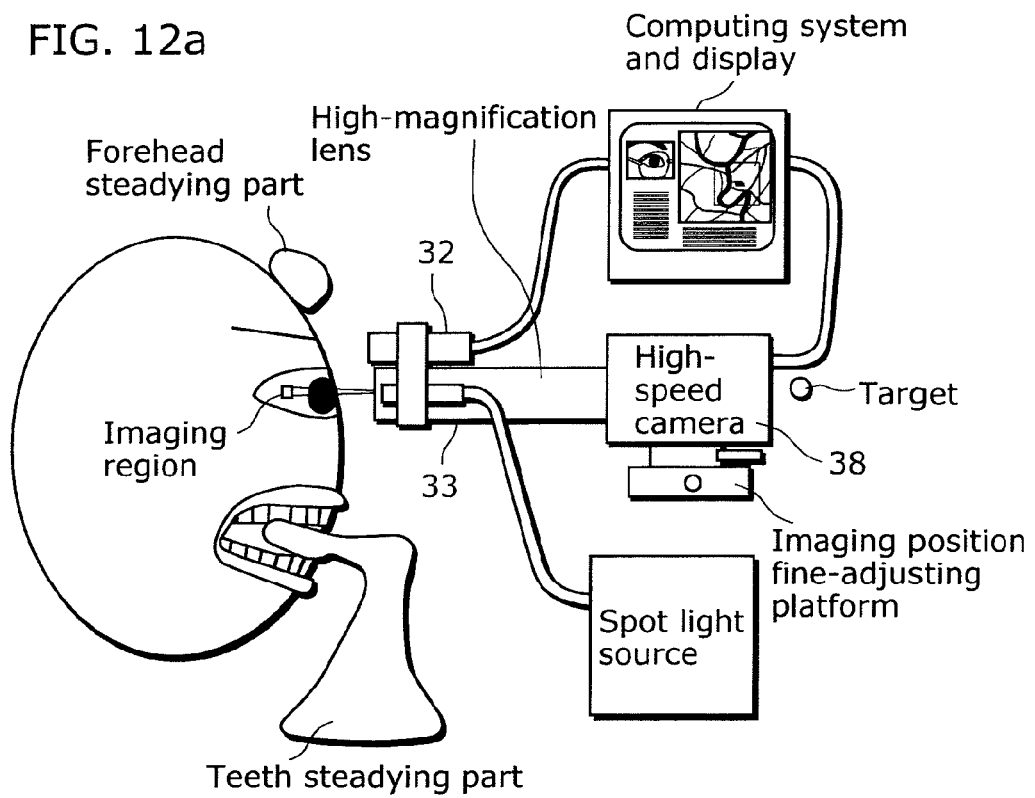
FIG. 12 is a configuration diagram of a measuring device for measuring fixational eye movement; (a) is a lateral view of the measuring device, and (b) is a bird's-eye view of the measuring device.
Figure 12B:
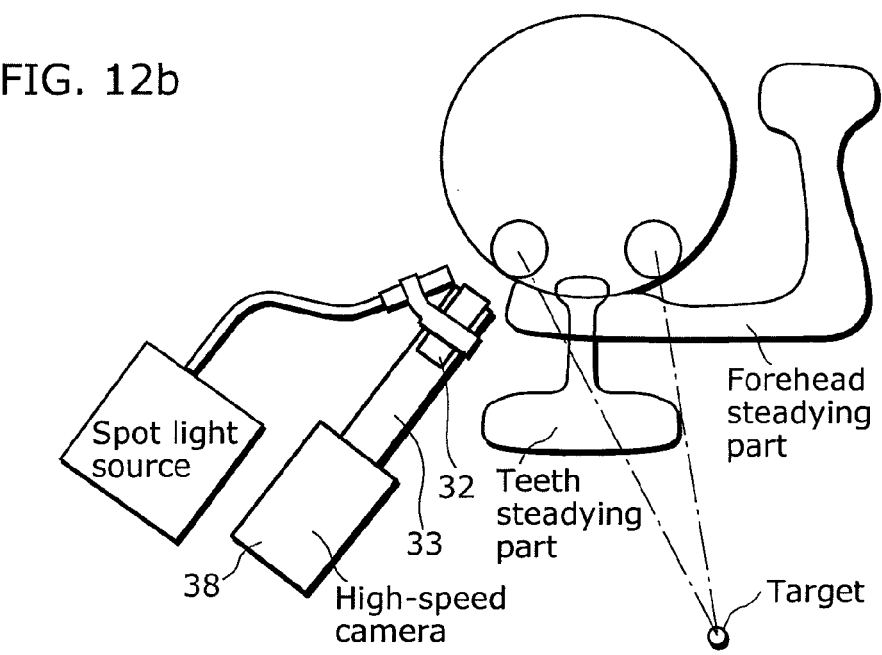

FIG. 12 is a configuration diagram of a measuring device used by the inventors for accurately measuring small eye movement among the eyeball movements. In FIG. 12, (a) is a lateral view and (b) is a bird's-eye view. This measuring device corresponds to another embodiment of the video obtaining unit 11 and the analyzing unit 12 of the human state estimating device 10 in the present invention.

Figure 13:
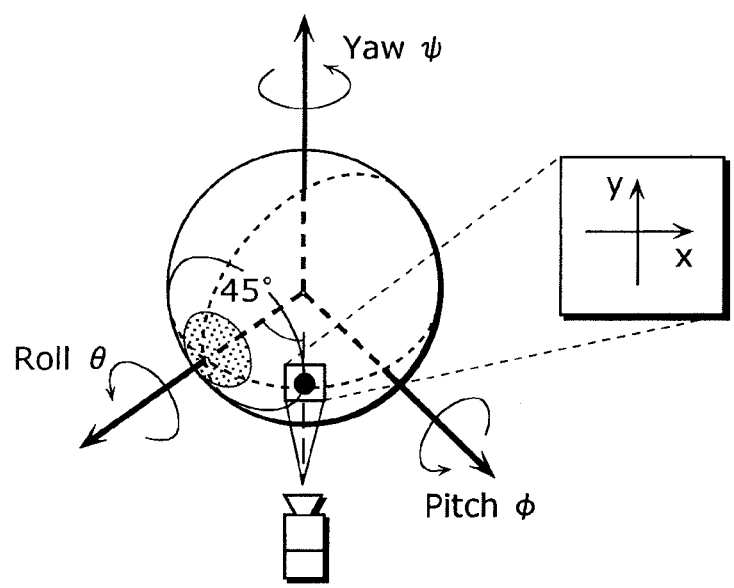
FIG. 13 is a diagram showing the relationship between the optical axis of a high-speed camera and the visual axis of an eyeball, in the measuring device.

The optical axis of a high-speed camera 88 equipped with a high-magnification lens 33 is set on an equatorial plane. The angle created by the optical axis of the high-speed camera 38 and the visual axis when the eyeball looks to the front is 45 degrees as shown in FIG. 13. Furthermore, a wide-angle lens-equipped camera 32 for measuring the overall position of the eyeball is provided. Since the wide-angle camera 32 and the high-speed camera 38 are fixed with respect to one another, by taking overall images of an eye from the wide-angle camera 32 and aligning the portion to be measured to a particular position of the wide-angle camera images, the imaging region of the high-speed camera 38 can be aligned to that portion.

Figure 14:
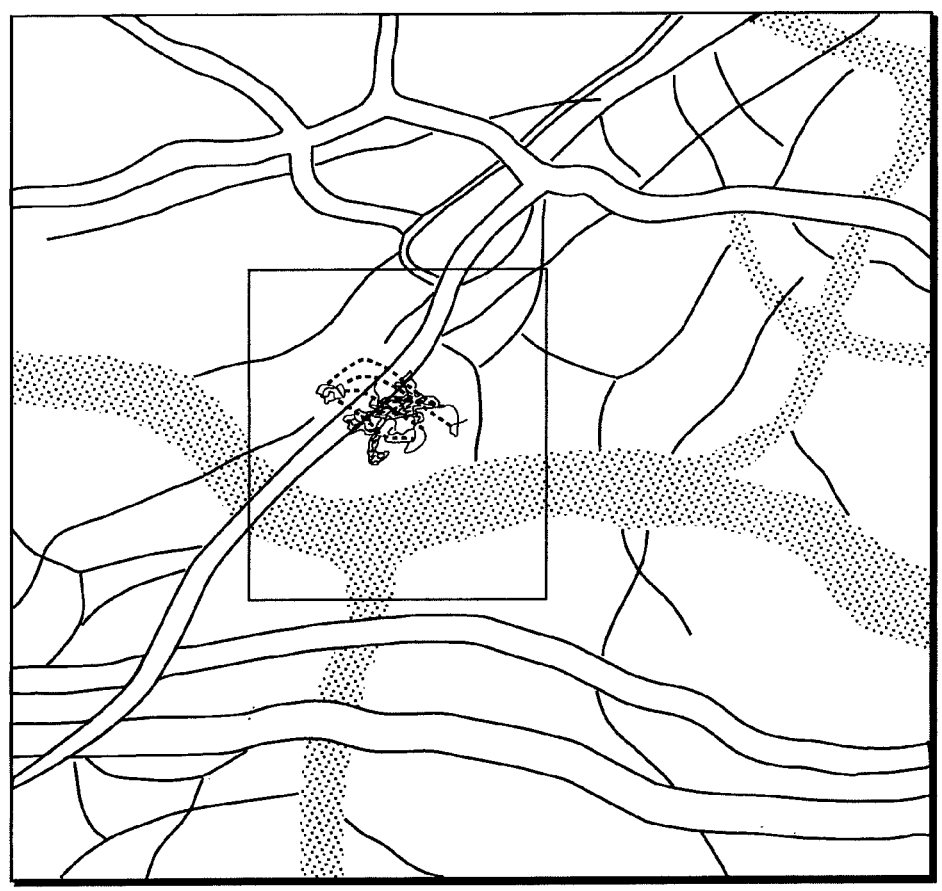
FIG. 14 is a diagram showing an example of a movement trajectory of fixational eye movement.

In the present embodiment, the imaging speed of the high-speed camera 38 was set to 250 frames/second, and a 4.5× magnification lens was used for the lens. FIG. 14 is a diagram showing an example of a sclera image (movement trajectory of fixational eye movement) taken from a camera. In FIG. 14, the square frame is the region of a block-matching pattern. A solid line and a dotted line in the square frame are eyeball movement trajectories discovered through block-matching, and indicate the trajectory of a drift and a microsaccade, respectively.

Figure 15A:
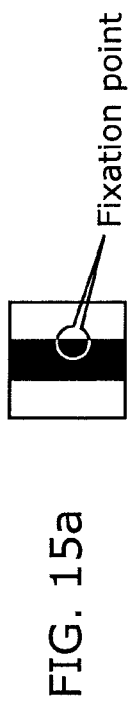
FIG. 15 is a diagram for describing time variation of the horizontal component and the vertical component of the fixational eye movement; (a) is a diagram showing a measuring condition for a target and a fixation point, and (b) is a diagram showing time variation of the horizontal component and the vertical component of movement in the fixational eye movement.
Figure 15B:
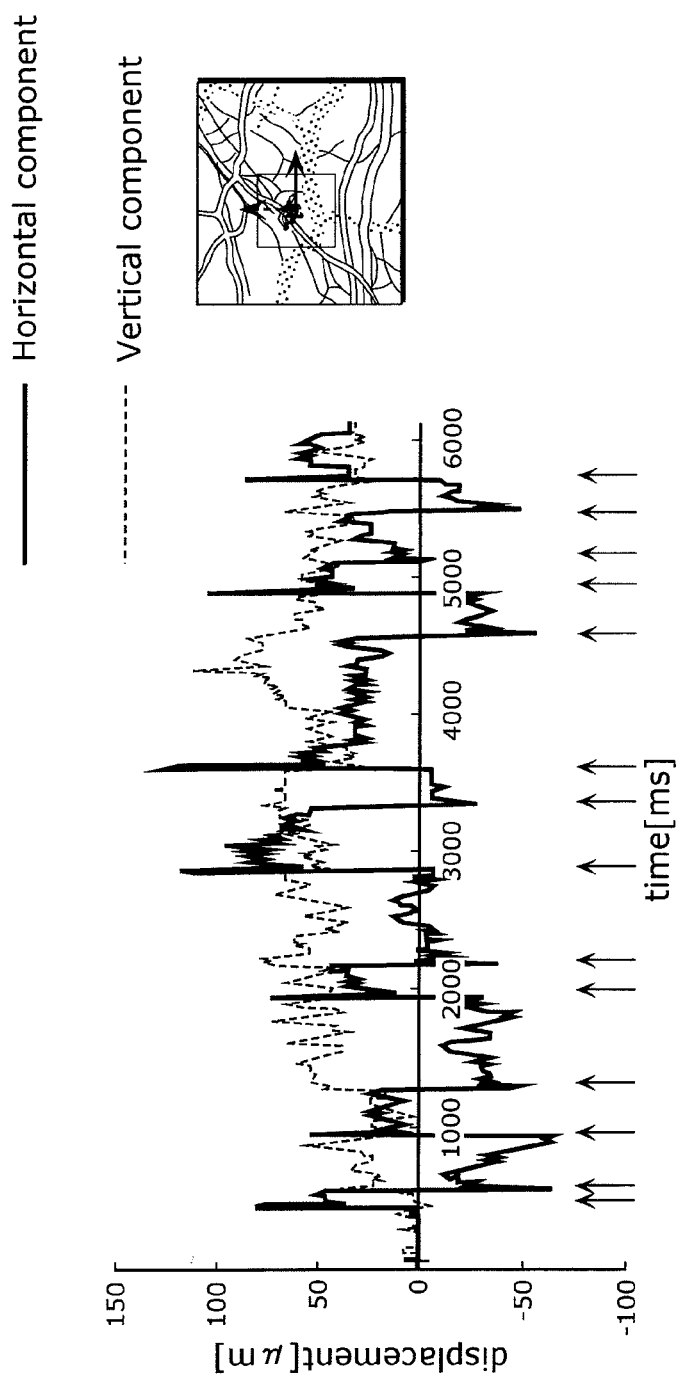

FIG. 15 is a diagram for describing the time variation of the horizontal component and the vertical component of fixational eye movements that have been measured. In FIG. 15, (a) is a diagram showing a measuring condition for a target (distance is 750 mm) and a fixation point, and (b) is a diagram showing the time variation of the horizontal component (solid line) and the vertical component (dotted line) of the movement (displacement [μm]) in the fixational eye movement. As can be understood from the figure, the horizontal eyeball movement and the vertical eyeball movement have different movement patterns, and microsaccades, which have a high movement speed, are mainly concentrated in the horizontal eyeball movement. In the graph of the vertical component shown in (b) in FIG. 15, the places where a large movement instantaneously occurs denotes microsaccades (more accurately, the horizontal component of a microsaccade). The occurrence frequency of a microsaccade is 2.33 Hz on average, and the movement amount is 120.6 μm on average.

FIG. 16 is a diagram for describing the correlation of mental state and a microsaccade. In FIG. 16, (a) is a diagram showing the measuring conditions for a target (a checkered pattern with a distance of 1.0 m, and a viewing angle of 2 degrees), (b) shows normal fixational eye movement when the subject is not given any orders, and (c) shows the fixational eye movement trajectory when the subject is counting prime numbers. As can be seen by comparing (b) and (c) in FIG. 16, the microsaccade movement range clearly increases when the subject is counting prime numbers.

With this, it is understood that, in the vertical component of the fixational eye movement, the frequency component (the vertical axis in FIG. 15 and FIG. 16) at the frequency (for example, a constant frequency width mainly at 2.33 Hz, and 2 to 3 Hz as a specific example) corresponding to the cycle typically observed as a microsaccade changes significantly depending on a thinking state such as counting prime numbers, and so on. It should be noted that it has been revealed that, aside from such thinking states, the movement amount of the microsaccade also changes depending on psychological states such as composure, uncertainty, and so on, and emotional states such as pleasure/displeasure, excitement/calmness, nervousness/relaxation, and so on. In addition, it has been revealed that, aside from microsaccades, other fixational eye movement (drift, tremor) and other eyeball movement (pupil diameter, and so on) also change depending on a human state such as the psychological state, the emotional state, and the thinking state. Therefore, the human state can be estimated based on such fixational eye movement or eyeball movement information.

Next, the significance of using information regarding eyeball movement, particularly the pupil, in order for the human state estimating device 10 in the present invention to estimate a human state and generate personal attribute information shall be described.

It is said that, even when the same experimental task load is applied, different results are obtained in physiological measurement data including eyeball movement or psychological data, depending on the age bracket or differences among individuals. Consequently, the inventors measured the psychological state and pupil diameter during the execution of a task in which auditory stimulus is used, and studied the correspondence between the two.

Figure 17:
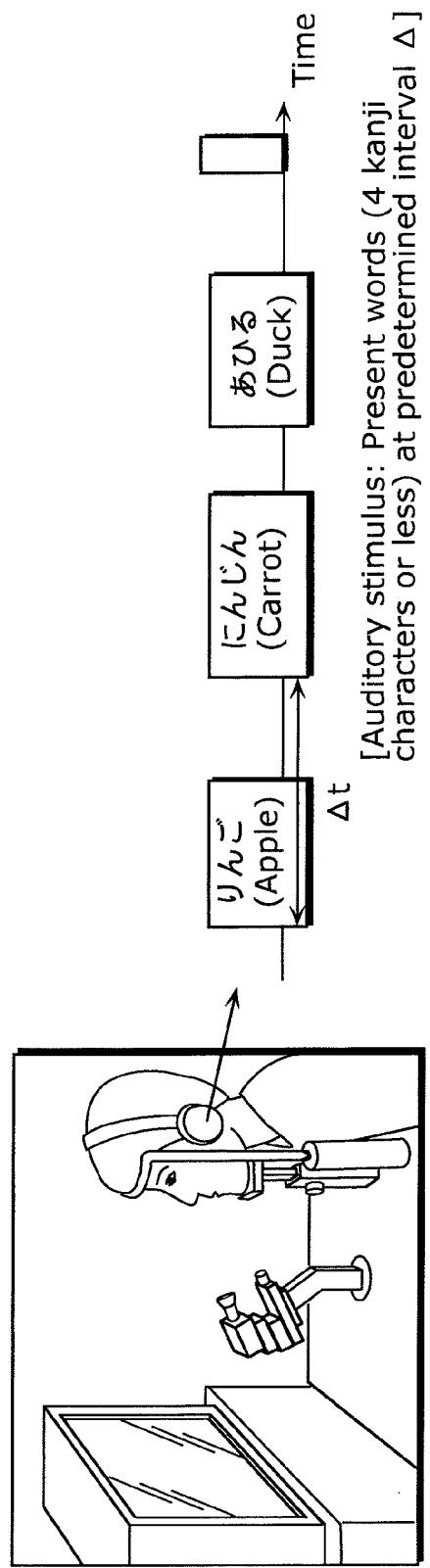
FIG. 17 is a diagram showing details of a pupil measuring experiment.
Figure 18D:
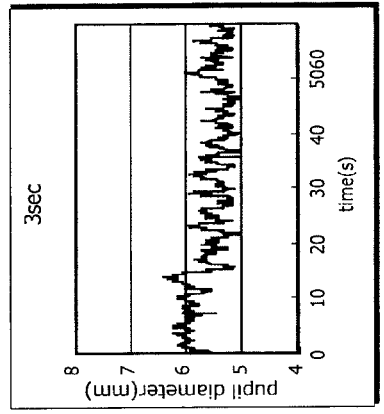
FIG. 18 is a diagram showing an example of data for the variation of pupil diameter; (a) is a diagram showing baseline data, and (b) to (d) are diagrams showing data when stimulus presentation interval is at 1 SEC, 2 SEC, and 3 SEC, respectively.
Figure 18A:
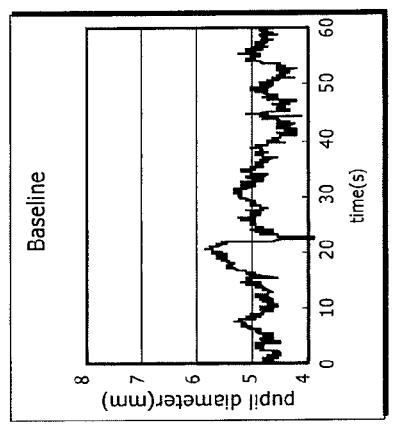
Figure 18C:
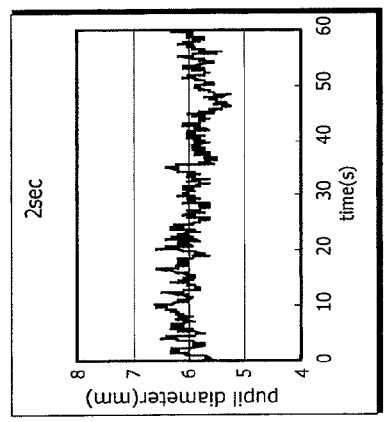
Figure 18B:
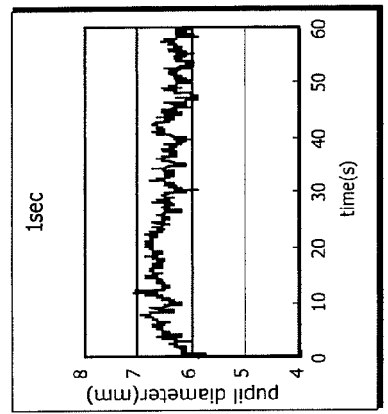

FIG. 17 shows the details of a pupil measuring experiment in the present embodiment. Auditory stimulus is presented to the subject through headphones. The main experiment conditions are as shown below.

(Condition 1) The subject answers, using a button, whether or not the presented stimulus belongs to a specified category.

(Condition 2) One trial is set for 60 seconds.

(Condition 3) The subjects fixes his gaze at a cross in the center.

(Condition 4) The stimulus presentation interval (Δt) is assumed as a parameter.

(Condition 5) A self-report of the psychological state is performed after one trial.

FIG. 18 is a diagram showing data samples of the variation in pupil diameter of the subject. In FIG. 18, (a) shows baseline data, and shows the variation in the pupil diameter when only auditory stimulus is received, without performing the task, in the aforementioned (condition 1), of answering, using the button, whether or not the auditory stimulus belongs to the specified category. In FIG. 18, (b) to (d) show data of 1 SEC, 2 SEC, 3 SEC, respectively, and show the measurement result for the pupil diameter variation when the stimulation presentation interval in the aforementioned (condition 4) is changed from 1 second to 2 seconds to 3 seconds, respectively. As can be seen from the baseline shown in (a) in FIG. 18, compared to when the task load in the aforementioned (condition 1) is present, the swinging of the pupil diameter variation frequency is moderate, and settles down in a line from 4 mm to 6 mm. However, as can be seen from (b) to (d) in FIG. 18, when the task load in the aforementioned (condition 1) is applied, the swinging shifts to 6 mm to 7 mm when the stimulus interval in the aforementioned (condition 4) is at 1 second, and to 5.5 mm to 6.5 mm at 2 seconds, and to 5 mm to 6 mm at 3 seconds. When the stimulus presentation interval is shortened, the pupil diameter increases, and there is a greater tendency for distraction at a 1 second interval than at 3 seconds, and sympathetic nerves are activated more than at the baseline.

Figure 19:
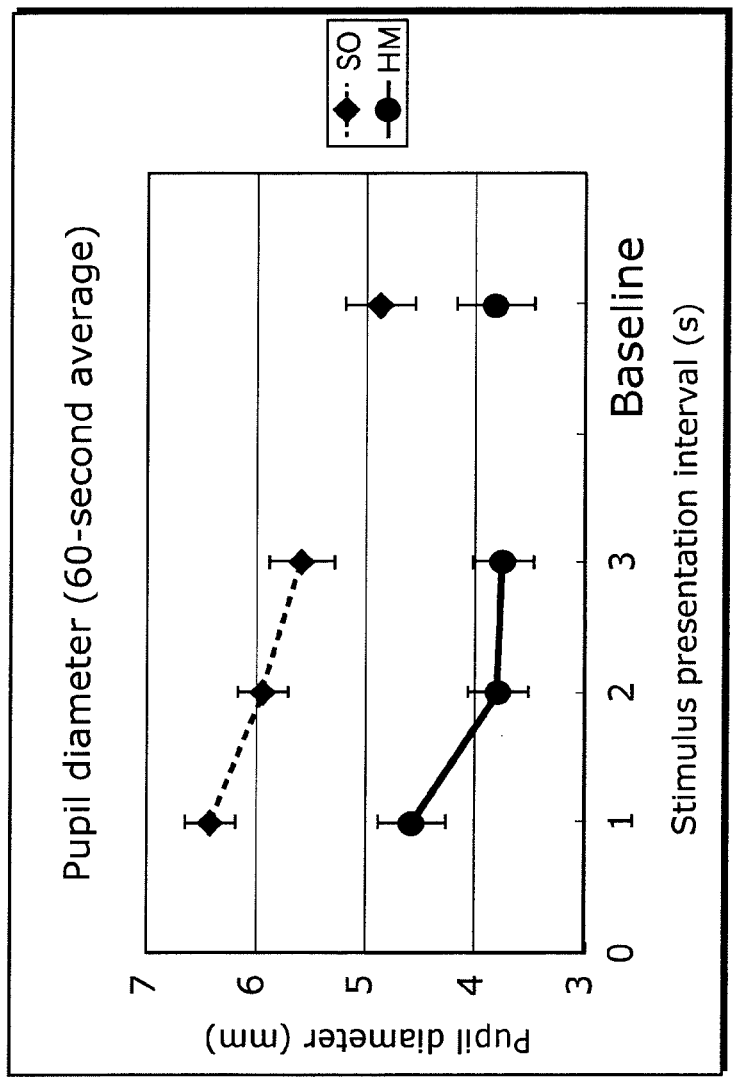
FIG. 19 is a diagram showing an example of differences among individuals in the variation of pupil diameter.

FIG. 19 is a diagram showing an example of differences among individuals in the variation of pupil diameter. Here, the average (60 second average) time variation of the pupil diameter during task execution for two persons, that is, a subject 1 (SO) and a subject 2 (HM) is illustrated. It should be noted that both the subjects are in their twenties. For both subject 1 and subject 2, the average of the pupil diameter becomes shorter and approaches the baseline, as the stimulus presentation interval becomes longer. Although it is said that, in general, the pupil diameter variation width is different for the twenties age bracket and the fifties age bracket, the variation curve is different for each person even in the same age bracket.

Figure 20A:
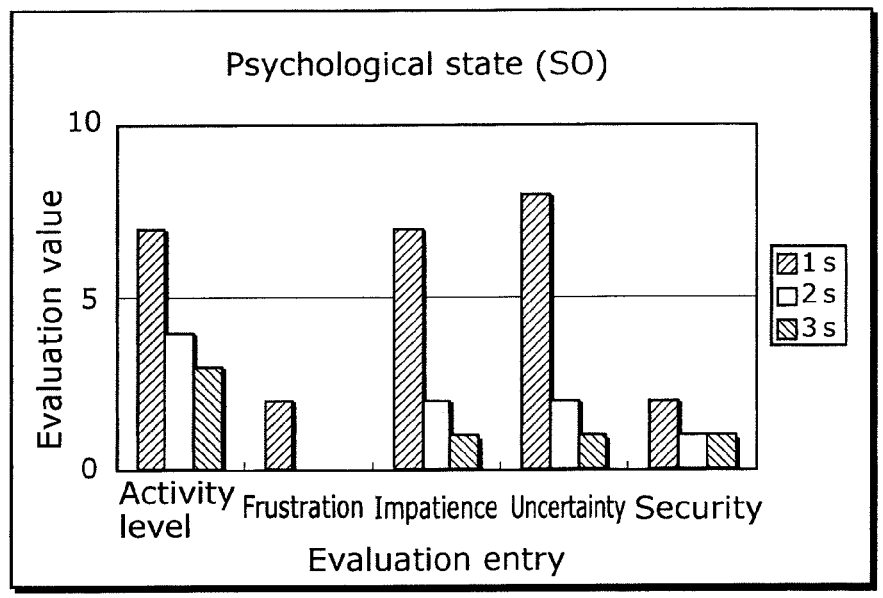
FIG. 20 is a diagram showing an example of differences among individuals in the variation of pupil diameter in various psychological states; (a) is a diagram showing data of the psychological state of subject 1, and (b) is a diagram showing the psychological state of subject 2.
Figure 20B:
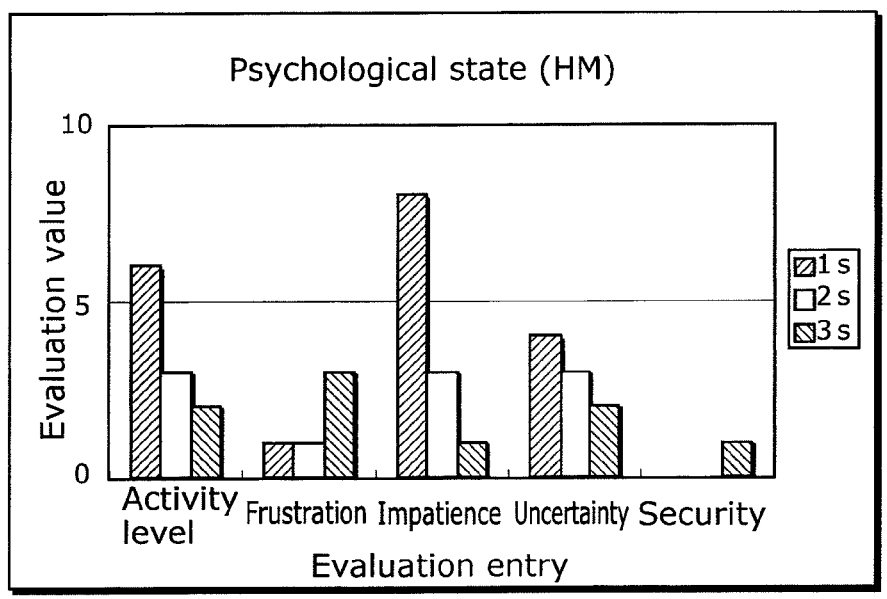

FIG. 20 is a diagram showing an example of differences among individuals in the variation of pupil diameter in the various psychological states. In FIG. 20, (a) is a diagram showing data summarizing the psychological state of subject 1 (SO) according to the aforementioned (condition 5), and (b) is a diagram showing data summarizing the psychological state of subject 2 (HM) according to the aforementioned (condition 5). As can be seen from the respective diagrams, activity level, impatience, and anxiety increases, for both subject 1 and subject 2, as the stimulus presentation interval in aforementioned (condition 4) becomes shorter. However, the vibration amplitudes are different depending on the subject. For example, with regard to uncertainty, at 1 second, in which there is a feeling of being under time pressure, subject 1 felt a high level of uncertainty whereas subject 2 felt an intermediate level of uncertainty. Furthermore, frustration was felt by subject 1 at 1 second but not at 2 seconds and 3 seconds. Inversely, frustration was not significantly felt by subject 2 at 1 second and 2 seconds, but felt at 3 seconds.

As described above, by using various information regarding pupil diameter, it is possible to estimate the human state, and identify personal attributes using differences among individuals with regard to pupil diameter.

It should be noted that the value for the pupil diameter in the reference profile 17*c* shown in FIG. 5 or for the eye movement information generated by the eyeball movement analyzing unit 12*b* may be a power value of the low frequency component or the high frequency component obtained as a result of performing power spectrum analysis of raw data indicating the pupil diameter variation shown in FIG. 18, for example. Furthermore, representation using the average value or a value of a slope, and so on, of the graph shown in FIG. 19 is also possible. Furthermore, as shown in FIG. 20, since there are cases where a psychological state indicated by one pupil variation data indicates plural psychological states (frustration, impatience, uncertainty, and so on), the actual-measurement profile, the reference profile, and the eyeball movement information may be identified, and the human state may be estimated/the personal attribute information may be determined, from the result of multiple regression analysis of a psychological data evaluation value and a performance spectrum analysis result. Furthermore, eyeball movement may be obtained not only through pupil diameter, but also by combining fixational eye movement and saccades.

As described above, according to the human state estimating device in the present embodiment, the human state is estimated accurately compared to the conventional estimation of the human state based simply on eyeball movement (or fixational eye movement) since the human state is estimated based on the fixational eye movement of an eyeball, particularly the horizontal component of a microsaccade which has a high correlation with the human state, and the human state is estimated by making use of the similarity of personal attributes, in addition to the eyeball movement. Specifically, with the biological information including eyeball movement which is said to be easily influenced by age bracket or illness state, and also has significant variation in differences among individuals and intra-personal differences, it is possible to use measured biological information and accurately estimate the mental state, which also includes unconsciousness, the thinking state, and the physical state of the user. As such, together with enabling the construction of an accurate quantitative and objective HMI evaluation system, the safety, amenity, and convenience of system devices is improved.

Furthermore, since the human state estimating device in the present invention uses information on eyeball movement (dynamic characteristics of fixational eye movement, saccades, ocular following responses, and pupil diameter) which are thought to be deeply related to autonomic nerves, it is possible to accurately derive a relational expression between the dynamic characteristics of an eyeball movement factor and a particular psychological state, such as uncertainty, irritation, impatience, confusion, bewilderment, and so on, which is the cause of stress during AV device operation, or negative and positive emotions including delight, anger, sorrow, and pleasure, or a mental disorder.

Furthermore, the measuring of eyeball movement is non-invasive as compared to most biological information measuring including brain wave measuring, and thus the mental/physical burden on the user can be reduced.

In addition, in the present invention, since it is possible to extract information for identifying an individual from capillary images in the sclera images, and perform person authentication by retrieving iris information from cornea images, there is no need for the user to directly input information for identifying personal attributes through the input unit each time, and thus convenience is improved. Furthermore, there is no need to add a new authenticating device, and thus an individual's mental and economic burden can be reduced.

Furthermore, when new personal attribute or new human state information is obtained, the human state estimating device in the present embodiment can register this as reference data to be used later in estimating, and thus excels in flexibility and expandability.

As described above, the present invention accurately estimates the human state, and thus the practical value of the present invention is extremely high particularly in this age where, together with increased functionality of electronic devices, the use situation and usage pattern of a user has become diversified.

Although the human state estimating device in the present invention has been described thus far based on an embodiment and modifications, the present embodiment is not limited to such embodiment and modifications. Other modifications implemented by combining arbitrarily selected constituent elements from the aforementioned embodiment and modifications, as well as variations to the aforementioned embodiment and modifications conceived by a person of ordinary skilled in the art are included in the present invention as long as they do not depart from the essence of the present invention.

For example, although the human state estimating device in the present invention is applied by being built into a television in the present embodiment, aside from a television, the human state estimating device may be applied by being built into a household appliance and in-vehicle device such as a personal computer, a car navigation device, and a mobile phone, or a monitoring device, a health management device, an air conditioning management device, and so on, used in homes and so on.

Furthermore, although in the present embodiment, the estimating unit 15 calculates and aggregates the degree of coincidences with the reference profiles for all of the eyeball movement parameters making up the actual-measurement profile, the present invention is not limited to searching in such manner. For example, a priority may be provided for each eyeball movement parameter making up the reference profile, and the degree of coincidence for each eyeball movement parameter may be aggregated after multiplying the degree of coincidences by a weighting coefficient conforming to the priority. With this, accurate human state estimation matching actual conditions becomes possible by increasing the priority of eyeball movement parameters that change significantly depending on human states.

Furthermore, although the value for visual acuity is stored in the "visual acuity" in the personal attribute information, information for identifying the state (abnormality) of the refracting system/modulating system of an eye such as myopia, hyperopia, astigmatism, and so on may be stored. This is because, such information is useful as supplementary parameters which improve the accuracy of human state estimation since even such information influences the relationship between personal attributes and the human state.

INDUSTRIAL APPLICABILITY

The present invention is useful: as a human state estimating device which measures the eyeball movement of a user and accurately estimates the state of the user, for example, as an electronic device (a household appliance, in-vehicle appliance such as a personal computer, car navigation device, mobile phone, and so on) provided with a screen such as a television, or as a device built into a monitoring device, a health management device, an air conditioning management device, and so on, used in homes and so on; or as a program for implementing the human state estimating device, and particularly as a customized HMI, device, or diagnostic device which also accommodates the problem of the digital divide.

The invention claimed is:

1. A human state estimating device which estimates a human state which is at least one of a psychological state, an emotional state, and a thinking state, based on fixational eye movement of an eyeball of a user, said human state estimating device comprising:
   a storage unit configured to store reference data in which a human state and a reference profile are corresponded to each other, for each of plural personal attribute information, the personal attribute information indicating at least one of an age bracket, visual acuity, and illness state of a person, and the reference profile including a horizontal component which is a left-right direction component of the eyeball in a microsaccade included in normal fixational eye movement of the eyeball in the human state;
   a video obtaining unit configured to obtain video showing movement of the eyeball including the fixational eye movement of the eyeball of the user, the video being obtained with an eyeball rotation angle accuracy of 0.05 degrees or higher and at a measuring speed of 120 samples per second or higher;
   an analyzing unit configured to extract a horizontal component of a microsaccade from the fixational eye movement shown in the video, and to generate an actual-measurement profile including the extracted horizontal component;
   a personal attribute information obtaining unit configured to obtain personal attribute information of the user via an input unit operated by the user, the personal attribute information of the user being (i) information that is self-reported by the user and (ii) information describing a personal attribute of the user which is not measured by the human state estimating device; and
   an estimating unit configured to search the reference data stored in said storage unit for a reference profile which corresponds to the personal attribute information obtained by said personal attribute information obtaining unit and which is closest to the actual-measurement profile, and to determine, as the human state estimated for the user, a human state corresponding to the searched-out reference profile, the human state estimated for the user being at least one of a psychological state, an emotional state, and a thinking state.

2. The human state estimating device according to claim 1, wherein the reference profile includes, as the horizontal component of the microsaccade, a frequency component at a frequency corresponding to a cycle that is typically observed as the microsaccade in the horizontal component of the fixational eye movement, and
   wherein said analyzing unit is configured to perform frequency analysis of time variation of the horizontal component of the fixational eye movement shown in the video, and to calculate, as the horizontal component of the microsaccade, a frequency component in a frequency spectrum obtained in the frequency analysis.

3. The human state estimating device according to claim 1, wherein the reference profile further includes information regarding at least one of a drift and a tremor, which are fixational eye movements,
   wherein said analyzing unit is configured to extract information regarding at least one of a drift and a tremor, from the fixational eye movement shown in the video, and to generate the actual-measurement profile including the extracted information, and
   wherein said estimating unit is configured to search for the reference profile that is closest to the actual-measurement profile by referring to the information regarding at least one of the drift and the tremor, in addition to the horizontal component of the microsaccade.

4. The human state estimating device according to claim 1, wherein the reference profile further includes information regarding pupil diameter,
   wherein said analyzing unit is configured to extract information regarding pupil diameter from the video, and to generate the actual-measurement profile including the extracted information, and
   wherein said estimating unit is configured to search for the reference profile that is closest to the actual-measurement profile by referring to the information regarding the pupil diameter, in addition to the horizontal component of the microsaccade.

5. The human state estimating device according to claim 1, wherein said analyzing unit is configured to further analyze, based on the video obtained by said video obtaining unit, eyeball movement including at least one of line of sight, line of sight trajectory, line of sight stationary time, convergence and divergence, fixational eye movement dynamic characteristics, saccade dynamic characteristics, pupil diameter, and pupil dynamic characteristics of the user, and wherein said personal attribute information obtaining unit has a personal attribute table indicating a correspondence relationship between the eyeball movement and the personal attribute information, and is configured to identify, by referring to the personal attribute table, personal attribute information corresponding to a result of the analysis of the eyeball movement by said analyzing unit, and to obtain the identified personal attribute information as the personal attribute information of the user.

6. The human state estimating device according to claim 1, further comprising a registering unit configured to obtain information for identifying the human state of the user, and to register, as new reference data, the obtained information, the personal attribute information obtained by said personal attribute information unit for the user, and the actual-measurement profile generated by said analyzing unit, corresponding to each other.

7. The human state estimating device according to claim 1, wherein said personal attribute information obtaining unit is configured to obtain an age bracket of the user from the user via the input unit, and wherein said estimating unit is configured to search the reference data stored in said storage unit for a reference profile which corresponds to the age bracket of the user obtained by said personal attribute information obtaining unit and which is closest to the actual-measurement profile.

8. A human state estimating method executed by a human state estimating device which estimates a human state which is at least one of a psychological state, an emotional state, and a thinking state, based on fixational eye movement of an eyeball of a user, wherein the human state estimating device includes a storage unit configured to store reference data in which the human state and a reference profile are corresponded to each other, for each of plural personal attribute information, the personal attribute information indicating at least one of an age bracket, visual acuity, and illness state of a person, and the reference profile including a horizontal component which is a left-right direction component of the eyeball in a microsaccade included in normal fixational eye movement of the eyeball in the human state, said human state estimating method comprising:

obtaining video which shows movement of the eyeball including the fixational eye movement of the eyeball of the user, the video being obtained with an eyeball rotation angle accuracy of 0.05 degrees or higher and at a measuring speed of 120 samples per second or higher;

extracting a horizontal component of a microsaccade from the fixational eye movement shown in the video, and generating an actual-measurement profile including the extracted horizontal component;

obtaining personal attribute information of the user via an input unit operated by the user, the personal attribute information of the user being (i) information that is self-reported by the user and (ii) information describing a personal attribute of the user which is not measured by the human state estimating device; and searching the reference data stored in the storage unit for a reference profile which corresponds to the personal attribute information obtained in said obtaining personal attribute information and which is closest to the actual-measurement profile, and determining, as the human state estimated for the user, a human state corresponding to the searched-out reference profile, the human state estimated for the user being at least one of a psychological state, an emotional state, and a thinking state.

9. A non-transitory computer readable recording medium having stored thereon a program for a human state estimating device which estimates a human state which is at least one of a psychological state, an emotional state, and a thinking state, based on fixational eye movement of an eyeball of a user, wherein the human state estimating device includes a storage unit configured to store reference data in which the human state and a reference profile are corresponded to each other, for each of plural personal attribute information, the personal attribute information indicating at least one of an age bracket, visual acuity, and illness state of a person, and the reference profile including a horizontal component which is a left-right direction component of the eyeball in a microsaccade included in normal fixational eye movement of the eyeball in the human state, and wherein, when executed, said program causes the human state estimating device to perform a human state estimating method comprising:

obtaining video which shows movement of the eyeball including the fixational eye movement of the eyeball of the user, the video being obtained with an eyeball rotation angle accuracy of 0.05 degrees or higher and at a measuring speed of 120 samples per second or higher;

extracting a horizontal component of a microsaccade from the fixational eye movement shown in the video, and generating an actual-measurement profile including the extracted horizontal component;

obtaining personal attribute information of the user via an input unit operated by the user, the personal attribute information of the user being (i) information that is self-reported by the user and (ii) information describing a personal attribute of the user which is not measured by the human state estimating device; and searching the reference data stored in the storage unit for a reference profile which corresponds to the personal attribute information obtained in said obtaining personal attribute information and which is closest to the actual-measurement profile, and determining, as the human state estimated for the user, a human state corresponding to the searched-out reference profile, the human state estimated for the user being at least one of a psychological state, an emotional state, and a thinking state.

* * * * *